(12) United States Patent  
Ma et al.

(10) Patent No.: US 11,737,977 B2  
(45) Date of Patent: Aug. 29, 2023

(54) CERASOME DELIVERY SYSTEM FOR TARGETING ACTIVATED CD44 MOLECULE, PREPARATION METHOD AND USE THEREOF

(71) Applicant: Beijing Inno Medicine Co., Ltd., Beijing (CN)

(72) Inventors: Qian Ma, Beijing (CN); Jiefang Sun, Beijing (CN)

(73) Assignee: Beijing Inno Medicine Co., Ltd., Beijing (CN)

( * ) Notice: Subject to any disclaimer, the term of this patent is extended or adjusted under 35 U.S.C. 154(b) by 99 days.

(21) Appl. No.: 16/605,120

(22) PCT Filed: Apr. 12, 2018

(86) PCT No.: PCT/CN2018/082850  
§ 371 (c)(1),  
(2) Date: Apr. 2, 2020

(87) PCT Pub. No.: WO2018/188635  
PCT Pub. Date: Oct. 18, 2018

(65) Prior Publication Data  
US 2021/0145747 A1 May 20, 2021

(30) Foreign Application Priority Data  
Apr. 12, 2017 (CN) .......................... 201710236679.8

(51) Int. Cl.  
*A61K 9/127* (2006.01)  
*A61P 9/00* (2006.01)  
(Continued)

(52) U.S. Cl.  
CPC ............ *A61K 9/1272* (2013.01); *A61K 9/127* (2013.01); *A61K 45/06* (2013.01); *A61P 9/00* (2018.01); *G01N 33/5436* (2013.01)

(58) Field of Classification Search  
None  
See application file for complete search history.

(56) References Cited

U.S. PATENT DOCUMENTS

2002/0131995 A1 9/2002 Szoka  
2009/0035348 A1* 2/2009 Zadini .................... A61K 38/44  
424/423

(Continued)

FOREIGN PATENT DOCUMENTS

CN 105708800 A 6/2016  
CN 106177982 A 12/2016  
(Continued)

OTHER PUBLICATIONS

Cao Z, Ma Y, Yue X, Li S, Dai Z, Kikuchi J. Stabilized liposomal nanohybrid cerasomes for drug delivery applications. Chemical communications. 2010;46(29):5265-7. (Year: 2010).*

(Continued)

*Primary Examiner* — Nissa M Westerberg  
(74) *Attorney, Agent, or Firm* — Fox Rothschild LLP

(57) ABSTRACT

A cerasome delivery system for targeting activated cd44 molecule, a preparation method and use thereof: a surface of a cerasome is partially modified by a targeting ligand, the targeting ligand being a ligand which may specifically bind to an activated cd44 molecule. The cerasome delivery system may be used for the diagnosis, prevention and treatment of vulnerable plaque or diseases associated with vulnerable plaque.

9 Claims, 11 Drawing Sheets

(51) Int. Cl.
*A61K 45/06* (2006.01)
*G01N 33/543* (2006.01)

(56) References Cited

U.S. PATENT DOCUMENTS

| 2012/0107229 | A1* | 5/2012 | Huang | A61K 47/6923 424/1.11 |
|---|---|---|---|---|
| 2012/0116064 | A1 | 5/2012 | Dai et al. | |

FOREIGN PATENT DOCUMENTS

| JP | 2011020923 A | 2/2011 | | |
| WO | 2007102253 A1 | 9/2007 | | |
| WO | 2010120905 A2 | 10/2010 | | |
| WO | WO-2015031536 A1 * | 3/2015 | | A61P 25/00 |
| WO | 2019141275 A1 | 7/2019 | | |

OTHER PUBLICATIONS

Jin Y, Ma X, Feng S, Liang X, Dai Z, Tian J, Yue X. Hyaluronic acid modified tantalum oxide nanoparticles conjugating doxorubicin for targeted cancer theranostics. Bioconjugate chemistry. Dec. 16, 2015;26(12):2530-41. (Year: 2015).*

Liang X, Gao J, Jiang L, Luo J, Jing L, Li X, Jin Y, Dai Z. Nanohybrid liposomal cerasomes with good physiological stability and rapid temperature responsiveness for high intensity focused ultrasound triggered local chemotherapy of cancer. ACS nano. Feb. 24, 2015;9(2):1280-93. (Year: 2015).*

Lee RJ, Low PS. Folate-mediated tumor cell targeting of liposome-entrapped doxorubicin in vitro. Biochimica et Biophysica Acta (BBA)-Biomembranes. Feb. 15, 1995;1233(2):134-44. (Year: 1995).*

Kawataki T, Yasuhara K, Kikuchi JI. Remarkable Long-term Stability of Cerasome as an Organic-Inorganic Hybrid Nanocontainer for Water-soluble Macromolecules. Chemistry letters. May 5, 2011;40(5):461-3. (Year: 2011).*

Mishra PK, Gulbake A, Jain A, Vyas SP, Jain SK. Targeted delivery of an anti-cancer agent via steroid coupled liposomes. Drug delivery. Nov. 1, 2009;16(8):437-47. (Year: 2009).*

"Lipids For Liposome Formation" from https://avantilipids.com/tech-support/liposome-preparation/lipids-for-liposome-formation, accessed Jan. 12, 2023 (Year: 2023).*

Kolodgie et al., "Differential Accumulation of Proteoglycans and Hyaluronan in Culprit Lesions Insights Into Plaque Erosion," Arterioscler Thromb Vasc. Biol. (2002); 22: 1642-1648.

Liu et al., "Hyaluronic acid-decorated reconstituted high density lipoprotein targeting atherosclerotic lesions," Biomaterials (2014); 35: 8002-8014.

"Research Status of CD44 Molecule," Int. J. Respir. (2006); 26(12): 938-942.

* cited by examiner (a)

(b)

(a)

(b)

Imaging of antibody-cerasome nuclear magnetic contrast

Imaging of ligand-cerasome nuclear magnetic contrast
(each carrier group is encapsulated with 0.5 MG/ML of gadodiamide)

CERASOME DELIVERY SYSTEM FOR TARGETING ACTIVATED CD44 MOLECULE, PREPARATION METHOD AND USE THEREOF

CROSS REFERENCE TO RELATED APPLICATIONS

The present application is a national application of PCT/CN2018/082850 filed on Apr. 12, 2018, which claims the priority of the Chinese Patent Application No. 201710236679.8 filed on Apr. 12, 2017. The Chinese Patent Application No. 201710236679.8 is incorporated herein by reference as part of the disclosure of the present application.

TECHNICAL FIELD

The present disclosure belongs to the technical field of targeted drug delivery, and in particular relates to a cerasome delivery system for targeting an activated CD44 molecule, especially for targeting a vulnerable plaque. The present disclosure further relates to a preparation method of the cerasome delivery system and use of the cerasome delivery system, particularly in the diagnosis, prevention and treatment of a vulnerable plaque or a disease associated with the vulnerable plaque.

BACKGROUND OF THE INVENTION

At present, acute cardiovascular events, mainly including acute myocardial infarction and sudden cardiac death, have become the number one threat for human health. According to statistics, about 20 million people die from acute cardiovascular events worldwide each year. The situation in China is also not optimistic. More than 700,000 people die from acute myocardial infarction and sudden cardiac death each year, which has become one of the most notable diseases that seriously threaten the health of the Chinese people. Studies have shown that most of the acute myocardial infarction and sudden cardiac death are caused by atherosclerotic plaques. Since the 1970s, the process and mechanism in which a chronic atherosclerotic plaque leads to acute coronary syndrome (ACS) and stroke have been explored constantly.

In 1989, Muller and colleagues (Circadian Variation and Triggers of Onset of Acute Cardiovascular Disease. *Circulation.* 1989; 79(4): 733-43) proposed the concept of "vulnerable plaque", presuming that such a plaque is the fundamental cause of most of the acute cardiovascular and cerebrovascular events. A vulnerable plaque (also known as "unstable plaque") refers to an atherosclerotic plaque that tends to form thrombus or is likely to progress rapidly into "criminal plaque", including rupture-prone plaque, erosion-prone plaque and partially calcified nodular lesions. A large number of studies have shown that most of the acute myocardial infarction and stroke are caused by the rupture of vulnerable plaques having mild to moderate stenosis, followed by thrombosis. Naghavi and colleagues (New Developments in the Detection of Vulnerable plaque. *Curr Atheroscler Rep.* 2001; 3(2): 125-35) et al. provided the histological definition and criteria for the vulnerable plaque. The main criteria include active inflammation, thin fibrous caps and large lipid cores, endothelial exfoliation together with platelet aggregation on the surface, plaque fissures or lesions, and severe stenosis. Secondary criteria include calcified plaques on the surface, yellow and lustrous plaques, intraplaque hemorrhage, and positive remodeling. Therefore, early intervention is critical for the vulnerable plaque. However, as the degree of vascular stenosis caused by the vulnerable plaque is normally not so high that many patients have no prodromal symptoms, the early diagnosis of the vulnerable plaque in clinical is very difficult, making the vulnerable plaque extremely dangerous. Therefore, an urgent problem to be solved in the prevention and treatment of acute myocardial infarction is how to accurately identify and diagnose a vulnerable plaque as early as possible, so that an effective intervention can be carried out.

Currently, the commonly used techniques for the diagnosis of a vulnerable plaque mainly include coronary angiography, intravascular ultrasound (IVUS), optical coherence tomography (OCT), etc., but these techniques are all invasive examination with low diagnostic resolution and accuracy, and high expenses, which limits the clinical use of these techniques to some extent. Therefore, currently, there is an urgent need for non-invasive diagnostic techniques and preparations for the vulnerable plaque.

In addition, the current method of treating a vulnerable plaque is mainly via systemic administration, such as oral administration of statins (hydroxymethyl glutaryl coenzyme A (HMG-CoA) reductase inhibitors), aspirin, matrix metalloproteinases (MMPs) inhibitors and/or fibrates, etc. These drugs act to stabilize plaques by reducing lipids in plaques, improving vascular remodeling, etc through regulating systemic blood fats, fighting inflammation, inhibiting proteases and platelet production, etc. However, in clinical applications, it has been found that the therapeutic effects of current drugs for treating vulnerable plaques are not satisfactory. For example, the statins commonly used in clinical practice have relatively low bioavailability when administered orally, such as <5% for simvastatin, about 12% for atorvastatin, and about 20% for rosuvastatin. Animal experiments have also confirmed that only when the dose of statins is increased to more than 1 mg/kg can they increase the thickness of the fibrous cap and reduce the volume of plaques, which makes the stability of oral administration of statins and their effect of reversing plaques encounter a bottleneck. At present, clinical trials have also confirmed that the treatment of vulnerable plaques by oral administration of statins requires intensive large doses to stabilize the vulnerable plaques, while treatment with systemic large doses of statins also has a risk of increased incidence of serious side effects (such as abnormal liver function, rhabdomyolysis, type II diabetes, etc.).

For existing systemic administration, usually only a very small portion of active ingredients can actually act on a lesion site after a drug enters the body. This is the fundamental cause that limits the efficacy of the drug and produces toxic side effects. A targeted drug delivery system refers to a drug delivery system that has the ability of targeted drug delivery. After administered via a certain route, the drug contained in the targeted drug delivery system is specifically enriched in a targeted site by a carrier with a targeting probe. The targeted drug delivery system is capable of making the drug targeting to a particular lesion site and releasing the active ingredients at the target lesion site. Therefore, the targeted drug delivery system may result in a relatively high concentration of the drug in the target lesion site, and a reduced dose of the drug in the blood circulation, thereby improving the drug effect while suppressing toxic side effects, and reducing damage to normal tissues and cells.

At present, nanocarriers commonly used in the targeted drug delivery system are liposomes. Although liposomes have the advantages of improving the drug effect and reducing the toxic side effects of the drug, liposomes have limited ability to increase the bioavailability of the drug due to poor stability in vivo and thus insufficient circulation time. In addition, the stability of the liposomes in vitro is also insufficient, readily leading to oxidation and hydrolyzation of the phospholipid during storage, and the liposome vesicles are easily aggregated and fused to each other, readily resulting in the leakage problem of the drug enclosed therein. These problems all limit the development of the targeted drug delivery system to some extent.

In addition, in the field of diagnosis and treatment of vulnerable plaques, there are also some techniques for diagnosing the vulnerable plaques by modifying the nanocarriers with targeting ligands. However, a major problem of such targeting probes, which target vulnerable plaques, in clinical practice is the insufficient specificity of these preparations to targeted sites. For example, for most of such preparations, macrophages are selected as the targeted sites; however, since macrophages are present throughout the body, the targeting specificity of the probes is not satisfactory. Therefore, the difficulty in the development of targeting preparations which target vulnerable plaques lies in the discovery of targeted sites with significant targeting specificity in cells within the vulnerable plaques.

CD44 is a type of adhesive molecules that are widely distributed on the surface of lymphocytes, monocytes, endothelial cells, etc. The main ligand of the CD44 molecule is hyaluronic acid (abbreviated as "HA"). Based on the activation state of cells expressing CD44, CD44 can exist in a relatively static state (which cannot bind to HA), an induced activation state (which can bind to HA after activation), and a structurally active state (which can bind to HA without activation), while CD44 on the surface of most normal cells are in the relatively static state and cannot bind to HA.

A number of previous studies have shown that CD44 is not an ideal targeted sites with significant targeting specificity. This is because CD44 is widely distributed in the human body, especially on the surface of organs rich in reticuloendothelial. Therefore, the following problem will be encountered in the development of the targeted drug delivery system using CD44 as the targeted sites: if the CD44 on the surface of targeted cells has insufficient affinity to HA to provide significant specificity, such a targeted drug delivery system will not have specifically targeting properties.

Therefore, finding specific targeted sites present at vulnerable plaques and targeted drug delivery systems suitable for targeting vulnerable plaques, thereby developing a targeted drug delivery system capable of specifically targeting vulnerable plaques while achieving stable and sustained release of the drug, has become an urgent technical problem to be solved in the medical field.

To date, there is no report on the expression status of CD44 on the surface of macrophages, monocytes, endothelial cells, lymphocytes and smooth muscle cells mainly present within vulnerable plaques or on their affinity for HA, and there is no any prior art regarding designing a targeted drug delivery system for diagnosing or treating the vulnerable plaques or a disease associated with the vulnerable plaques while achieving stable and sustained release of the drug by utilizing the interaction between HA and CD44 and the specific microenvironment of the vulnerable plaques either.

SUMMARY OF THE INVENTION (1) Overview of the Invention

The present inventors have found that as compared to normal cells, CD44 on the surface of cells, such as endothelial cells, macrophages, and smooth muscle cells, in vulnerable plaques is activated by the specific microenvironment (such as inflammatory factors) of the vulnerable plaques, and therefore their binding ability to HA is suddenly increased by dozens of times. This finding suggests that a large number of activated CD44 molecules present on the surface of cells at vulnerable plaques provide ideal targeted sites for the targeted drug delivery system with HA as a targeting ligand. To this end, the present disclosure provides a targeted drug delivery system for specifically targeting an activated CD44 molecule, especially for targeting a vulnerable plaque.

The present inventors have also discovered that a large amount of lipids such as cholesterol are present at vulnerable plaques, which can act as emulsifiers, will seriously affect the stability of liposomes in the common targeted drug delivery system; as a result, the liposomes is rapidly disintegrated for being destroyed or eroded (extracted), which causes the drug encapsulated in the liposomes to be released ahead of schedule, failing to achieve the sustained release of the drug. However, if an advanced nanocarrier instead of a liposome is used in the drug delivery system, the release characteristics of the encapsulated drug at the vulnerable plaques will be significantly improved without being affected by lipid erosion, while maintaining good stability in the microenvironment at the vulnerable plaques, enabling sustained release of the drug. To this end, the present disclosure also provides a targeted drug delivery system capable of specifically targeting vulnerable plaques while enabling stable and sustained release of the drug.

The present inventors have also discovered that loading with a CD44 activator can promote the further activation of CD44 on the surface of the lesion cells, and can amplify the targeting affinity of CD44 for HA in a short time, which significantly increases the concentration of targeting cerasome compositions bound to the cell surface, showing active significance for the tracer diagnosis and treatment of vulnerable plaques. To this end, the targeted drug delivery system of the present disclosure can be simultaneously loaded with a CD44 activator, which can significantly increase the concentration of a tracer or therapeutic agent compound in a short period of time to improve diagnostic sensitivity or therapeutic effect.

The present inventors have also found that in vulnerable plaques, along with the high level of activation and over expression of CD44, the endogenous macromolecular HA is generated in a large quantity by stimulation, which binds to CD44 on the cell surface, promoting aggregation of cells such as macrophages and lymphocytes in the vulnerable plaques. Such an endogenous HA, which binds to CD44 on a cell surface, can form a barrier to drug entry and reduce the bioavailability of the drug. To this end, the targeted drug delivery system of the present disclosure can be loaded with a small-molecular hyaluronic acid or a hyaluronic acid derivative capable of specifically binding to a CD44 molecule on a cell surface at the vulnerable plaque, which eliminates the barrier formed by the endogenous HA on the cell surface by competing the binding of the endogenous HA on the cell surface, facilitating the successful intracellular release of the drug in the lesion cells and providing a significant therapeutic effect.

In summary, the present disclosure relates to the following aspects:

The present disclosure provides a cerasome delivery system for targeting an activated CD44 molecule.

The present disclosure provides a cerasome delivery system for targeting a vulnerable plaque.

The present disclosure provides a method for preparing the cerasome delivery system of the present disclosure for targeting a vulnerable plaque.

The present disclosure further provides a medicament, comprising the cerasome delivery system of the present disclosure for targeting a vulnerable plaque and pharmaceutically acceptable carriers.

The present disclosure further provides a diagnostic preparation, comprising the cerasome delivery system of the present disclosure for targeting a vulnerable plaque.

The present disclosure further provides the use of the cerasome delivery system of the present disclosure for targeting a vulnerable plaque in the preparation of a medicament for preventing and/or treating the vulnerable plaque or a disease associated with the vulnerable plaque.

The present disclosure further provides the use of the cerasome delivery system of the present disclosure for targeting a vulnerable plaque in the preparation of a diagnostic preparation for diagnosing the vulnerable plaque or a disease associated with the vulnerable plaque.

The present disclosure further provides a method for preventing and/or treating the vulnerable plaque or a disease associated with the vulnerable plaque, wherein the method comprises administering the cerasome delivery system of the present disclosure for targeting a vulnerable plaque to a subject in need thereof.

The present disclosure further provides a method for diagnosing the vulnerable plaque or a disease associated with the vulnerable plaque, wherein the method comprises administering the cerasome delivery system of the present disclosure for targeting a vulnerable plaque to a subject in need thereof.

Specific embodiments of the technical solutions of the present disclosure and their meanings will be described in detail below.

(2) Technical Terms and Meanings Thereof

The terms mentioned herein have the following meanings:

The "vulnerable plaque" (also known as an "unstable plaque") refers to an atherosclerotic plaque that tends to form thrombus or is likely to progress rapidly into "criminal plaque", including rupture-prone plaque, erosion-prone plaque and partially calcified nodular lesions. A large number of studies have shown that most of the acute myocardial infarction and stroke are caused by the rupture of vulnerable plaques with mild to moderate stenosis, followed by thrombosis. Histological manifestations of the vulnerable plaque include active inflammation, thin fibrous caps and large lipid cores, endothelial exfoliation with surface platelet aggregation, plaque fissures or lesions, and severe stenosis, as well as calcified plaques on the surface, yellow and lustrous plaques, intraplaque hemorrhage, and positive remodeling.

The "disease associated with the vulnerable plaque" mainly refers to a disease associated with the "vulnerable plaque", characterized by the "vulnerable plaque", caused by the "vulnerable plaque" or secondary to the "vulnerable plaque" during the occurrence and development of the disease. The "disease associated with the vulnerable plaque" mainly includes atherosclerosis, coronary atherosclerotic heart disease (including acute coronary syndrome, asymptomatic myocardial ischemia—latent coronary heart disease, angina pectoris, myocardial infarction, ischemic heart disease, sudden death, and in-stent restenosis), cerebral arteriosclerosis (including stroke), peripheral vascular atherosclerosis (including carotid atherosclerosis, renal atherosclerosis, lower extremity atherosclerosis, and upper extremity atherosclerosis), aortic dissection, hemangioma, thromboembolism, heart failure, cardiogenic shock, etc.

The "targeted drug delivery system" refers to a drug delivery system that has the ability of targeted drug delivery. After administration via a certain route, the drug contained in the targeted drug delivery system is specifically enriched in the targeted site by the action of a special carrier or a targeting warhead (e.g., a targeting ligand). Currently known means for achieving targeted drug delivery include utilizing the passive targeting properties of various microparticle delivery systems, introducing chemical modification on the surface of microparticle delivery systems, utilizing some special physical and chemical properties, utilizing an antibody-mediated targeted drug delivery, utilizing a ligand-mediated targeted drug delivery, utilizing a prodrug targeted drug delivery, etc. Among others, the ligand-mediated targeted drug delivery combines a drug carrier with a ligand, which utilizes the characteristic that a specific receptor in certain organ and tissue specifically binds to its specific ligand, thereby directing the drug to a specific target tissue.

The "cerasome" is a novel structurally stable lipid bilayer vesicles developed in the late 1990s. The cerasome of the present disclosure is a delivery system of active substance, which is, morphologically, a closed vesicle formed by a lipid bilayer having an inner hydrophilic cavity. The lipid bilayer is formed by a lipid component including a ceramic lipid. The cerasomic lipid is an inorganic-organic hybrid lipid molecule capable of forming a cerasome, and the inorganic-organic hybrid lipid molecule is composed of a head having a siloxane structure and a hydrophobic tail, wherein the hydrophobic tail is a hydrophobic organic bimolecular chain. The cerasome monomer molecule is typically a trialkoxysilylated lipid which forms Si—O—Si bonds via an in situ sol-gel process, thereby forming an inherently rigid inorganic polysiloxane network on the surface of the cerasome. The cerasome delivery system for targeting the vulnerable plaques, as used herein, is a ligand-mediated targeted drug delivery system which is designed based on the finding that a large number of activated CD44 molecules present on the cell surface at vulnerable plaques specifically bind to HA.

The "hyaluronic acid (abbreviated as "HA")" is a polymer of a macromolecule and has the formula of $(C_{14}H_{21}NO_{11})_n$. It is a higher polysaccharide consisting of the units D-glucuronic acid and N-acetylglucosamine. D-glucuronic acids and N-acetylglucosamines are linked by β-1,3-glycosidic bonds, and the disaccharide units are linked by β-1,4-glycosidic bonds. Thanks to a unique molecular structure and physical and chemical property, the hyaluronic acid displays various important physiological functions in an organism, such as lubricating joints, regulating the permeability of blood vessel walls, regulating the diffusion and transportation of proteins, water, and electrolytes, and promoting wound healing. It is especially important that the hyaluronic acid has a special water retention effect and is the substance having the best moisture retention property found in nature.

The "derivative of the hyaluronic acid" as used herein refers to any derivative of the hyaluronic acid capable of retaining the ability of the hyaluronic acid for specifically binding to CD44 molecules on the surface of cells at vulnerable plaques, including, but not limited to, pharmaceutically acceptable salts of the hyaluronic acid, lower alkyl (alkyl containing 1 to 6 carbon atoms) esters, prodrugs capable of forming the hyaluronic acid by hydrolysis or other means in the body, etc. Judging whether a substance is a "derivative of the hyaluronic acid" can be achieved by measuring the ability of the substance for specifically binding to CD44 molecules on the cell surface at vulnerable plaques, which is within the skills of a person skilled in the art.

The "CD44 molecule" is a type of transmembrane proteoglycan adhesion molecules widely expressed on the cell membrane of cells such as lymphocytes, monocytes, and endothelial cells, consisting of three segments, i.e., an extracellular segment, a transmembrane segment, and an intracellular segment. The CD44 molecule can mediate a variety of interactions between cells and cells, and between cells and extracellular matrix, participate in the transmission of various signals in the body, and thus change the biological function of cells. The primary ligand for the CD44 molecule is hyaluronic acid, and the receptor-ligand binding of the CD44 molecule and the hyaluronic acid determines the adhesion and/or migration of cells in the extracellular matrix. In addition, the CD44 molecule is also involved in the metabolism of the hyaluronic acid.

"Alkyl" means a saturated aliphatic hydrocarbon group containing both a branched chain and a straight chain which have a specified number of carbon atoms. For example, "$C_{1-6}$ alkyl" means an alkyl group having 1, 2, 3, 4, 5 or 6 carbon atoms, such as methyl, ethyl, propyl, butyl, pentyl, hexyl, isopropyl, isobutyl, sec-butyl, tert-butyl, isopentyl, neopentyl, etc. Similarly, "$C_{10-24}$ alkyl" refers to an alkyl group having 10, 11, 12, 13, 14, 15, 16, 17, 18, 19, 20, 21, 22, 23 or 24 carbon atoms.

"Alkenyl" means an unsaturated aliphatic hydrocarbon group containing a straight or branched configuration which has a defined number of carbon atoms and one or more (preferably one to six, such as one, two, three, four, five or six) carbon-carbon double bonds (which may exist along the chain at any stable point). For example, "$C_{10-24}$ alkenyl" refers to an alkenyl group having 10, 11, 12, 13, 14, 15, 16, 17, 18, 19, 20, 21, 22, 23 or 24 carbon atoms, and one or more (preferably one to six, such as one, two, three, four, five or six) carbon-carbon double bonds.

"About" represents a set of all values within the range of ±5% of the numerical value given thereafter.

(3) Detailed Description of the Invention

According to an aspect of the present disclosure, the present disclosure provides a cerasome delivery system for targeting an activated CD44 molecule, wherein the surface of the cerasome is partially modified by a targeting ligand, and the targeting ligand is a ligand capable of specifically binding to the activated CD44 molecule.

According to an aspect of the present disclosure, the present disclosure provides a cerasome delivery system for targeting a vulnerable plaque, wherein the surface of the cerasome is partially modified by a targeting ligand, and the targeting ligand is a ligand capable of specifically binding to a CD44 molecule on a cell surface at the vulnerable plaque.

According to an aspect of the present disclosure, the present disclosure provides a cerasome delivery system for targeting a vulnerable plaque, wherein the cerasome delivery system comprises a cerasome vesicle, and wherein the surface of the cerasome vesicle is partially modified by a targeting ligand.

In an embodiment, the cerasome vesicle is a closed vesicle formed by a lipid bilayer having an inner hydrophilic cavity, and wherein the surface of the vesicle has an inorganic polysiloxane reticulate structure and a coupled targeting ligand.

In an embodiment, the lipid bilayer is formed by components including a cerasome monomer molecule, a distearoylphosphatidylethanolamine (DSPE) molecule coupled to a targeting ligand by a covalent bond, and optionally other lipid molecules.

In an embodiment, the weight ratio of the cerasome monomer molecule, the distearoylphosphatidylethanolamine (DSPE) molecule coupled to a targeting ligand by a covalent bond, and the optionally other lipid molecules is 1 to 10:0.2 to 1:1 to 9.

In an embodiment, the weight ratio of the cerasome monomer molecule, the distearoylphosphatidylethanolamine (DSPE) molecule coupled to a targeting ligand by a covalent bond, and the optionally other lipid molecules is 2 to 10:1 to 3:0 to 3.

In an embodiment, the weight ratio of the cerasome monomer molecule, the distearoylphosphatidylethanolamine (DSPE) molecule coupled to a targeting ligand by a covalent bond, and other lipid molecules is 3 to 7:1.5 to 2.5:1.5 to 2.5.

In an embodiment, the weight ratio of the cerasome monomer molecule, the distearoylphosphatidylethanolamine (DSPE) molecule coupled to a targeting ligand by a covalent bond, and other lipid molecules is 3 to 7:0.5 to 1:1.5 to 2.5.

In an embodiment, the weight ratio of the cerasome monomer molecule, the distearoylphosphatidylethanolamine (DSPE) molecule coupled to a targeting ligand by a covalent bond, and other lipid molecules is 4 to 6:0.5:2.

In an embodiment, the weight ratio of the cerasome monomer molecule, the distearoylphosphatidylethanolamine (DSPE) molecule coupled to a targeting ligand by a covalent bond, and other lipid molecules is 4 to 6:2:2.

In an embodiment, the cerasome monomer molecule is an inorganic-organic composite lipid molecule capable of forming a cerasome, and the inorganic-organic composite lipid molecule is composed of a head having a siloxane structure and a hydrophobic tail, wherein the hydrophobic tail is a hydrophobic organic bimolecular chain.

In an embodiment, the cerasome monomer molecule is a monomer molecule having the general structural formula as follows:

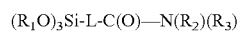

$(R_1O)_3Si-L-C(O)-N(R_2)(R_3)$ wherein:

$R_1$ represents $C_{1-6}$ alkyl;

L is a linker composed of 4 to 12 carbon atoms (preferably 4 to 10 carbon atoms) and 1 to 2 nitrogen atoms, wherein 0 to 1 carbon atom in the linker is substituted by an oxo group, i.e., a carbonyl group is formed, provided that (1) if a carbonyl group is present in the linker, the carbonyl group is adjacent to the nitrogen atom(s); and (2) 1 nitrogen atom in the linker can be quaternized, and the quaternized nitrogen atom can form a salt with a suitable counter ion; and $R_2$ and $R_3$ represent, independently of each other, $C_{10-24}$ alkyl or $C_{10-24}$ alkenyl.

In an embodiment, the cerasome monomer molecule is selected from one or more of the following compounds:

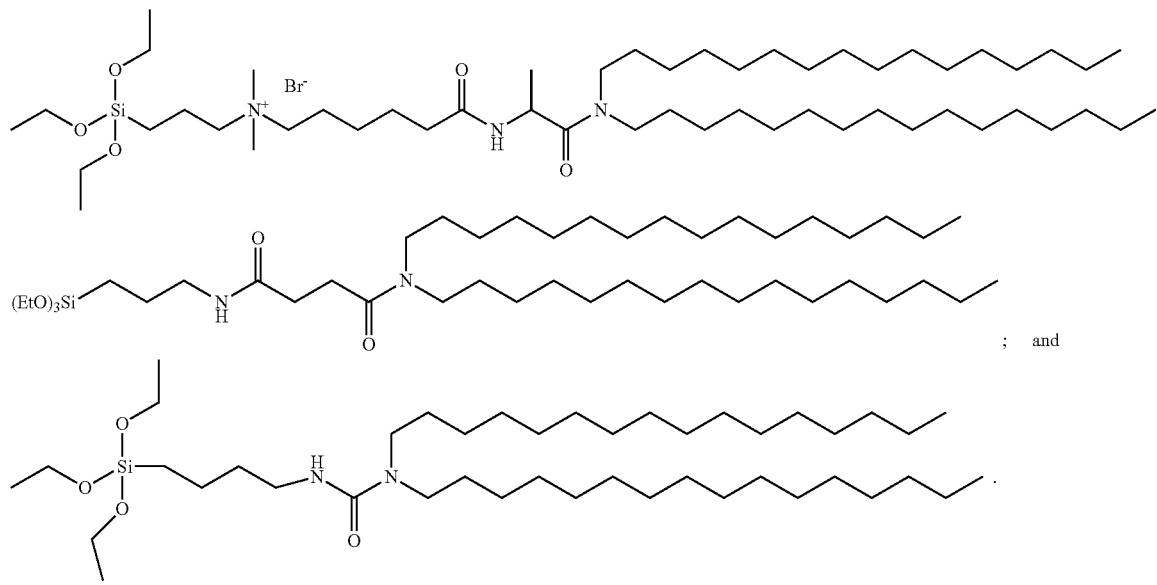

In an embodiment, the components of the lipid bilayer comprise other lipid molecules.

In an embodiment, the other lipid molecules are selected from one or more of neutral phospholipids, negatively-charged phospholipids and positively-charged lipids.

In an embodiment, the lipids are selected from one or more of phosphatidylcholine, glycerophospholipid, phosphatidylethanolamine, serine phosphatide, and phosphatidic acid.

In an embodiment, the other lipid molecules are phosphatidylcholine.

In an embodiment, the other lipid molecules are positively charged lipids.

In an embodiment, the positively-charged lipids are selected from one or more of 3β-[N—(N',N'-dimethylaminoethyl)carbamoyl]cholesterol (DC-chol), N-[1-(2,3-dioleoyloxy)propyl]-N,N,N-triethylammonium chloride (DOTMA), 2,3-dioleoyloxy-N-[2-(sperminecarboxamido) ethyl]-N,N-dimethyl-1-propanaminium trifluoroacetate (DOSPA) and 1,2-dioleoyloxypropyl-N,N,N-trimethylammonium bromide (DOTAP).

In an embodiment, the lipids are 1,2-dioleoyloxypropyl-N,N,N-trimethylammonium bromide (DOTAP).

In one embodiment, the targeting ligand has a molecular weight of 50,000-400,000 Da.

In one embodiment, the targeting ligand has a molecular weight of 80,000-150,000 Da.

In one embodiment, the targeting ligand has a molecular weight of about 100,000 Da.

In an embodiment, the particle size of the cerasome vesicle is in the range of 50 nm-400 nm.

In an embodiment, the particle size of the cerasome vesicle is in the range of 50 nm-300 nm.

In an embodiment, the particle size of the cerasome vesicle is in the range of 150 nm-250 nm.

In an embodiment, the particle size of the cerasome vesicle is in the range of 180 nm-220 nm.

In the cerasome delivery system of the present disclosure, the targeting ligand in the delivery system is selected from GAG, collagen, laminin, fibronectin, selectin, osteopontin (OPN), and monoclonal antibodies HI44a, HI313, A3D8, H90 and IM7, or is selected from a hyaluronic acid or a hyaluronic acid derivative capable of specifically binding to a CD44 molecule on a cell surface at the vulnerable plaque.

In the cerasome delivery system of the present disclosure, the cerasome is loaded with a substance for diagnosing, preventing and/or treating a disease associated with the presence of CD44 molecule activation.

In an embodiment, the cerasome is loaded with a substance for diagnosing, preventing, and/or treating the vulnerable plaque or a disease associated with the vulnerable plaque.

In an embodiment, the substance is one or more of a drug, peptide, nucleic acid and cytokine for diagnosing, preventing, and/or treating the vulnerable plaque or a disease associated with the vulnerable plaque.

In an embodiment, the substance is a substance for diagnosing the vulnerable plaque or a disease associated with the vulnerable plaque.

In an embodiment, the substance for diagnosing the vulnerable plaque or a disease associated with the vulnerable plaque is a tracer.

In an embodiment, the tracer is selected from a CT tracer and an MRI tracer.

In an embodiment, the CT tracer is selected from an iodine-based nanoscale contrast agent, gold-based nanoscale contrast agent, tantalum oxide-based nanoscale contrast agent, bismuth-based nanoscale contrast agent, lanthanide-based nanoscale contrast agent, or other tracers with a similar structure.

In an embodiment, the CT tracer is selected from iodinated contrast agent or nanogold, or other tracers with a similar structure.

In an embodiment, the CT tracer is selected from iohexol, iocarmic acid, ioversol, iodixanol, iopromide, iobitridol, iomeprol, iopamidol, ioxilan, acetrizoic acid, iodipamide, iobenzamic acid, ioglycamic acid, diatrizoic acid, sodium iotalamate, pantopaque, iopanoic acid, iodoalphionic acid, sodium acetrizoate, sodium iodomethamate, propyliodone, diodone, iotrolan, iopydol, endografin, iotalamic acid, meglumine diatrizoate, metrizoic acid, metrizamide, iodinated oil or ethiodized oil, or other tracers with a similar structure.

In an embodiment, the MRI tracer is selected from a longitudinal relaxation contrast agent and a transverse relaxation contrast agent.

In an embodiment, the MRI tracer is selected from a paramagnetic contrast agent, a ferromagnetic contrast agent and a superparamagnetic contrast agent.

In an embodiment, the MRI tracer is selected from Gd-DTPA and the linear, cyclic polyamine polycarboxylate chelate and manganese porphyrin chelate thereof, macromolecular gadolinium chelate, biomacromolecule-modified gadolinium chelate, folic acid-modified gadolinium chelate, dendrimer contrast agent, liposome-modified contrast agent and gadolinium-containing fullerene, or other tracers with a similar structure.

In an embodiment, the MRI tracer is selected from gadopentetate dimeglumine, gadoterate meglumine, gadobenate dimeglumine, gadodiamide, ferric ammonium citrate effervescent granules, paramagnetic iron oxide, or other tracers with a similar structure.

In the cerasome delivery system of the present disclosure, the cerasome is loaded with a CD44 activator. In an embodiment, the CD44 activator is a CD44 antibody mAb, or IL5, IL12, IL18, TNF-α, LPS.

In the cerasome delivery system of the present disclosure, the substance with which the cerasome is loaded is a small-molecular hyaluronic acid or a hyaluronic acid derivative capable of specifically binding to a CD44 molecule on a cell surface at the vulnerable plaque with a molecular weight in the range of 2,000-5,000 Da.

In an embodiment, the small-molecular hyaluronic acid or a hyaluronic acid derivative capable of specifically binding to a CD44 molecule on a cell surface at the vulnerable plaque has a molecular weight in the range of 2500-4500 Da.

In an embodiment, the small-molecular hyaluronic acid or a hyaluronic acid derivative capable of specifically binding to a CD44 molecule on a cell surface at the vulnerable plaque has a molecular weight in the range of 3000-4000 Da.

In an embodiment, the small-molecular hyaluronic acid or a hyaluronic acid derivative capable of specifically binding to a CD44 molecule on a cell surface at the vulnerable plaque has a molecular weight of about 3411 Da.

In the cerasome delivery system of the present disclosure, the cerasome is loaded with a substance for diagnosing, preventing, and/or treating the vulnerable plaque or a disease associated with the vulnerable plaque and a CD44 activator concurrently.

In the cerasome delivery system of the present disclosure, the cerasome is loaded with a substance for preventing and/or treating the vulnerable plaque or a disease associated with the vulnerable plaque, and a small-molecular hyaluronic acid or a hyaluronic acid derivative capable of specifically binding to a CD44 molecule on a cell surface at the vulnerable plaque with a molecular weight in the range of 2,000-5,000 Da concurrently.

In the cerasome delivery system of the present disclosure, the cerasome is loaded with a substance for diagnosing the vulnerable plaque or a disease associated with the vulnerable plaque, a substance for preventing and/or treating the vulnerable plaque or a disease associated with the vulnerable plaque, optionally, a CD44 activator, and optionally, a small-molecular hyaluronic acid or a hyaluronic acid derivative capable of specifically binding to a CD44 molecule on a cell surface at the vulnerable plaque with a molecular weight in the range of 2,000-5,000 Da, concurrently.

In the cerasome delivery system of the present disclosure, the substance with which the cerasome is loaded is a substance for preventing and/or treating the vulnerable plaque or a disease associated with the vulnerable plaque.

In an embodiment, the substance for preventing and/or treating the vulnerable plaque or a disease associated with the vulnerable plaque is selected from one or more of statins, fibrates, antiplatelet drugs, PCSK9 inhibitors, anticoagulant drugs, angiotensin converting enzyme inhibitors (ACEI), calcium ion antagonists, MNPs inhibitors, β receptor blockers, and the pharmaceutically acceptable salts thereof, including active structure fragments of the substances above.

In an embodiment, the substance for preventing and/or treating the vulnerable plaque or a disease associated with the vulnerable plaque is selected from lovastatin, atorvastatin, rosuvastatin, simvastatin, fluvastatin, pitavastatin, pravastatin, bezafibrate, ciprofibrate, clofibrate, gemfibrozil, fenofibrate, probucol, anti-PCSK9 antibodies such as evolocumab, alirocumab, bococizumab, RG7652, LY3015014 and LGT-209, antisense RNAi oligonucleotides such as ALN-PCSsc, nucleic acids such as microRNA-33a, microRNA-27a/b, microRNA-106b, microRNA-302, microRNA-758, microRNA-10b, microRNA-19b, microRNA-26, microRNA-93, microRNA-128-2, microRNA-144, microRNA-145 antisense strands and the nucleic acid analogs thereof such as locked nucleic acids, or adnectin such as BMS-962476, aspirin, acemetacin, troxerutin, dipyridamole, cilostazol, ticlopidine hydrochloride, sodium ozagrel, clopidogrel, prasugrel, cilostazol, tirofiban, beraprost sodium, ticagrelor, cangrelor, tirofiban, eptifibatide, abciximab, unfractionated heparin, clexane, fraxiparine, fondaparinux sodium, warfarin, dabigatran, rivaroxaban, apixaban, edoxaban, bivalirudin, enoxaparin, tedelparin, ardeparin, bishydroxycoumarin, nitrate coumarin, sodium citrate, hirudin, argatroban, benazepril, captopril, enalapril, perindopril, fosinopril, lisinopril, moexipril, cilazapril, perindopril, quinapril, ramipril, trandolapril, candesartan, eprosartan, irbesartan, losartan, telmisartan, valsartan, olmesartan or tasosartan, nifedipine, nicardipine, nitrendipine, amlodipine, nimodipine, nisoldipine, nilvadipine, isradipine, felodipine, lacidipine, diltiazem, verapamil, chlorhexidine, minocycline, MMI-166, metoprolol, atenolol, bisoprolol, propranolol, carvedilol, batimastat, marimastat, prinomastat, BMS-279251, BAY 12-9566, TAA211, AAJ996A, nacetrapib, evacetrapib, Torcetrapib and Dalcetrapib and the effective fragments or pharmaceutically acceptable salts thereof, and one or more of the pharmaceutically acceptable salts, including active structure fragments of the substances above.

In the cerasome delivery system of the present disclosure, the cerasome delivery system comprises a cerasome vesicle, wherein the surface of the cerasome vesicle is partially modified by a targeting ligand, and the targeting ligand is a hyaluronic acid or a hyaluronic acid derivative capable of specifically binding to a CD44 molecule on a cell surface at the vulnerable plaque.

The cerasome delivery system of the present disclosure for targeting the vulnerable plaque can be prepared according to any of the methods known in the art. For example, the cerasome delivery system of the present disclosure for targeting a vulnerable plaque is prepared by the thin-film dispersion method.

As a result, according to an aspect of the present disclosure, the present disclosure provides a method for preparing the cerasome delivery system of the present disclosure for targeting a vulnerable plaque, the method comprising the following steps:

1) dissolving an appropriate amount of a cerasome monomer molecule, a distearoylphosphatidylethanolamine (DSPE) molecule, the optionally other lipid molecules, and the optionally lipid-soluble substance for diagnosing, preventing, and/or treating the vulnerable plaque or a disease associated with the vulnerable plaque in a suitable organic solvent;
2) removing the organic solvent by means of rotary evaporation or under other appropriate conditions to allow the components of step 1) to form a thin-film on the wall of the vessel;
3) adding an aqueous medium optionally containing a water-soluble substance for diagnosing, preventing, and/or treating the vulnerable plaque or a disease associated with the vulnerable plaque, and fully hydrating the components in the film at a constant temperature of 40-60° C. so as to form a crude cerasome vesicle suspension;
4) treating the crude cerasome vesicle suspension obtained in step 3) by means of ultrasonication, shaking, homogenization, squeezing or other appropriate methods to obtain a refined cerasome vesicle suspension;
5) optionally removing the unloaded substance for diagnosing, preventing, and/or treating the vulnerable plaque or a disease associated with the vulnerable plaque contained in the refined cerasome vesicle suspension obtained in step 4) by means of dialysis;
6) placing the refined cerasome vesicle suspension obtained in step 4) or 5) for at least 24 hours to promote the hydrolytic condensation of siloxane to form an inorganic polysiloxane network;
7) under aqueous conditions, adding an appropriate amount of 1-(3-dimethylaminopropyl)-3-ethylcarbodiimide hydrochloride (EDC·HCl) and N-Hydroxysulfosuccinimide sodium salt (sulfo-NHS) coupling agent to activate the carboxyl group in the targeting ligand to give an activated targeting ligand;
8) adding the activated targeting ligand to the cerasome vesicle suspension obtained in step 6) to couple the activated targeting ligand to the distearoylphosphatidylethanolamine (DSPE) molecule via an amide bond formed therebetween to obtain the cerasome delivery system for targeting a vulnerable plaque.

According to an aspect of the present disclosure, the present disclosure provides a medicament, comprising the cerasome delivery system of the present disclosure and pharmaceutically acceptable carriers.

In an embodiment, the medicament comprises the cerasome delivery system of the present disclosure for targeting a vulnerable plaque and pharmaceutically acceptable carriers.

According to an aspect of the present disclosure, the present disclosure provides a diagnostic preparation, comprising the cerasome delivery system of the present disclosure for targeting a vulnerable plaque.

In an embodiment, the diagnostic preparation comprises the cerasome delivery system of the present disclosure for targeting a vulnerable plaque.

According to an aspect of the present disclosure, the present disclosure provides the use of the cerasome delivery system of the present disclosure in the preparation of a medicament for diagnosing, preventing and/or treating a disease associated with the presence of CD44 molecule activation.

In an embodiment, the present disclosure provides the use of the cerasome delivery system in the preparation of a medicament for diagnosing, preventing and/or treating the vulnerable plaque or a disease associated with the vulnerable plaque.

According to an aspect of the present disclosure, the present disclosure provides a method for diagnosing, preventing and/or treating a disease associated with the presence of CD44 molecule activation, wherein the method comprises administering the cerasome delivery system of the present disclosure.

In an embodiment, the present disclosure provides a method for diagnosing, preventing and/or treating the vulnerable plaque or a disease associated with the vulnerable plaque, wherein the method comprises administering the cerasome delivery system of the present disclosure.

In an embodiment, the vulnerable plaque is selected from one or more of rupture-prone plaque, erosion-prone and partially calcified nodular lesions.

In an embodiment, the disease associated with the vulnerable plaque is selected from one or more of coronary atherosclerotic heart disease, atherosclerosis, hemangioma, thromboembolism, angina pectoris, myocardial infarction, sudden cardiac death, heart failure, cardiogenic shock, ischemic cardiomyopathy, and stroke.

The present disclosure includes any combination of any of the above embodiments (including various preferred embodiments). In addition, for any given range, the present disclosure includes endpoint values of the range, any specific values within the range, and sub-ranges that are comprised of any two specific values within the range.

In summary, the cerasome delivery system of the present disclosure has the following advantages for a disease associated with the presence of CD44 molecule activation:
1) The cerasome delivery system of the present disclosure is capable of specifically binding to an activated CD44 molecule and enables stable and sustained release of the drug.
2) CD44 on the surface of cells in vulnerable plaques is activated by being induced by the extracellular matrix microenvironment, and is over expressed in a large amount, and the affinity of CD44-HA is significantly increased, so that the interaction between the CD44 in vulnerable plaques and HA has extremely significant affinity specificity. Thus, CD44 in the vulnerable plaques acts as excellent target of the cerasome delivery system of the present disclosure for targeting a vulnerable plaque.
3) The cerasome delivery system of the present disclosure for targeting a vulnerable plaque can actively target and enter the vulnerable plaque and bind to the focal cells. Thus, the cerasome delivery system can achieve the sustained release of the loaded substance at the lesion, significantly increasing and sustaining the concentration of the substance in the lesion area, and thereby improving the diagnostic or therapeutic effect of the delivery system.
4) The cerasome delivery system of the present disclosure for targeting a vulnerable plaque can encapsulate a small-molecular hyaluronic acid or a hyaluronic acid derivative capable of specifically binding to a CD44 molecule on a cell surface at the vulnerable plaque with a molecular weight in the range of 2,000-5,000 Da. The above-mentioned small-molecular hyaluronic acid and the derivative thereof eliminates the barrier formed by the endogenous hyaluronic acid on the cell surface by competing the binding of the endogenous hyaluronic acid on the cell surface, thereby facilitating the diagnostically or therapeutically active substance to successfully enter the lesion cells.

5) There is a huge lipid pool in the vulnerable plaque, which contains a large amount of oxidized low density lipoproteins (ox-LDLs). Liposomes are unstable in such an internal environment and are highly susceptible to disintegration, thus failing to achieve a controlled release function; whereas the cerasome delivery system of the present disclosure for targeting a vulnerable plaque is relatively stable in the lipid pool of vulnerable plaques and can release the drug continuously, thereby maintaining the drug concentration at the lesion.

6) The cerasome delivery system of the present disclosure for targeting a vulnerable plaque may also be loaded with a substance promoting the activation of CD44, namely a CD44 activator such as IL5, IL12, IL18, TNF-α, and LPS. Loading with a CD44 activator can promote the further activation of CD44 on the surface of the lesion cells, and can amplify the targeting affinity of CD44 for hyaluronic acid in a short time, which significantly increases the concentration of targeted cerasome composition bound to the cell surface, showing active significance for the tracer diagnosis and treatment of vulnerable plaques. The loading can significantly increase the concentration of a tracer or therapeutic agent compound in a short period of time to improve diagnostic resolution or therapeutic effect.

7) The cerasome delivery system of the present disclosure for targeting a vulnerable plaque has good mechanical stability, thermal stability and stability in a vulnerable plaque microenvironment, and has good storage stability; the cerasome monomer molecule contains Si—C and Si—O bonds, and such a chemical composition makes biodegradation thereof possible; the cerasome vesicles can be loaded with lipid-soluble substances, amphoteric compounds or water-soluble substances. By adjusting the degree of condensation and void of the inorganic polysiloxane network on the surface of the cerasome vesicles, the in vitro and in vivo release of the active substance can be controlled without destroying the morphological stability of the cerasome vesicles.

It is to be particularly noted that a person skilled in the art can implement the present disclosure by referring to the contents disclosed herein based on the state of the art. Moreover, a person skilled in the art can make similar improvements and equivalent substitutions to the present disclosure without departing from the spirit and scope of the present disclosure, and these similar improvements and equivalent substitutions will be apparent to a person skilled in the art and are intended to be included in the present disclosure. For example, substances that can be loaded in the cerasome delivery system of the present disclosure include, but are not limited to, those listed in the present disclosure, as long as they can be incorporated into the cerasome and can be used for purposes of diagnosis, prevention, and/or treatment. In general, as long as the substance is not a substance which is insoluble in both of the aqueous phase and the organic solvent or a substance which is very soluble in both of the aqueous phase and the organic solvent, it can be easily incorporated into the cerasome. Preferably, the substance is a lipid-soluble substance, an amphoteric compound or a water-soluble substance.

BRIEF DESCRIPTION OF THE DRAWINGS

To fully understand the content of the present disclosure, the present disclosure is further described in detail below by referring to the specific examples and the accompanying drawings, wherein.

DETAILED DESCRIPTION OF EMBODIMENTS

Figure 1:
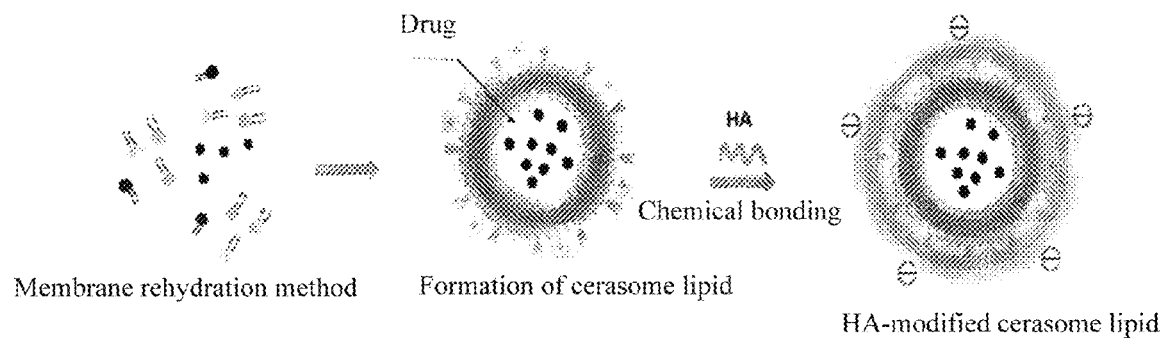
FIG. 1 is a schematic diagram for constructing the cerasome delivery system of the present disclosure for targeting a vulnerable plaque.

In order to further understand the present disclosure, the specific embodiments of the present disclosure are described in detail below with reference to the Examples. It is to be understood, however, that the descriptions are only intended to further illustrate the features and advantages of the present disclosure and are not intended to limit the claims of the present disclosure in any way.

Example 1: Three cerasome monomers used in the present disclosure

Cerasome monomers C1, C2 and C3 used in the cerasome delivery system of the present disclosure are known, which can be obtained according to the preparation methods as described in the reference documents.

The cerasome monomer C1: N,N-dicetyl-N$^a$-(6-((3-triethoxysilyl)propyl dimethylammonio)hexanoyl)alaninamide bromide; for the preparation thereof, see *Nature Protocols*, 2006, 1(3), 1227-1234

Example 2: Preparation of Delivery System

1. Preparation of Cerasome Delivery Systems HA-CL1@R, HA-CL2@R and HA-CL3@R which are Loaded with a Therapeutic Agent In this example, cerasome delivery systems HA-CL1@R, HA-CL2@R and HA-CL3@R, which are loaded with a therapeutic agent, are prepared by the thin-film dispersion method. The surfaces of the cerasome vesicles of the above three cerasome delivery systems are partially modified by the targeting ligand hyaluronic acid (abbreviated as "HA") and are loaded with rosuvastatin (represented by the abbreviation "R"), a substance for the prevention and/or treatment of the vulnerable plaque or a disease associated with the vulnerable plaque, and the only difference is that the cerasome monomer molecules used in the preparation of the three cerasome delivery systems are the cerasome monomers C1, C2 and C3 as described in Example 1, respectively.

The method for the preparation of the HA-CL1@R, HA-CL2@R and HA-CL3@R specifically comprises the following steps:

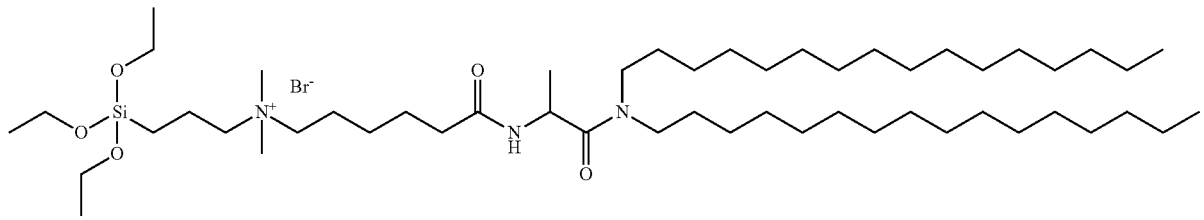

Molecular structure of the cerasome monomer C1

(1) Preparation of Cerasome Vesicle Suspension:

6 mg of C1 (5 mg of C2 or 4 mg of C3), 2 mg of 1,2-dioleoyloxypropyl-N,N,N-trimethylammonium bro- The cerasome monomer C2: N,N-dicetyl-N'-(3-triethoxysilylpropyl) succinamide; for the preparation thereof, see *J. Am, Chem. Soc.*, 2002, 124, 7892-7893

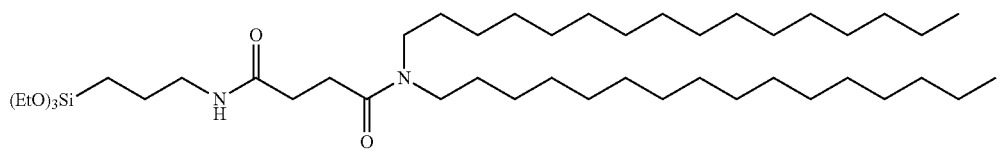

Molecular structure of the cerasome monomer C2

The cerasome monomer C3: N,N-dicetyl-N'-[(3-triethoxysilyl)propyl]urea; for the preparation thereof, see *Thin Solid Films*, 2003, 438-439, 20-26 mide (DOTAP) and 2 mg of distearoylphosphatidylethanolamine (DSPE) were weighed and dissolved with 10 mL of chloroform in a round bottom flask. The organic solvent

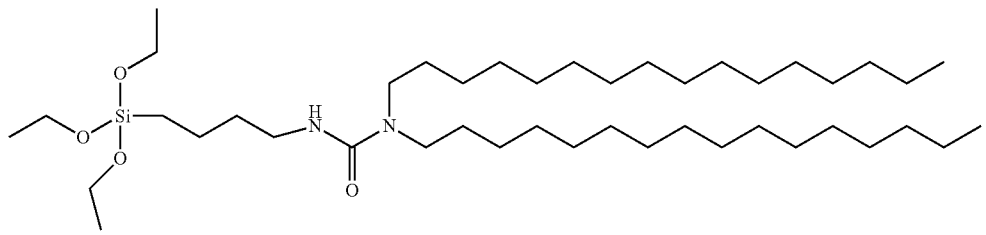

Molecular structure of the cerasome monomer C3 was completely removed by means of rotary evaporation (55° C. water bath, 90 r/min, 30 min) to form a thin-film on the wall of the flask. 10 mL rosuvastatin aqueous solution was added (at a concentration of 2 mg/mL), and the flask was placed in a constant-temperature water bath kettle at 50° C. to fully hydrate the thin-film for 30 min, so as to form a crude cerasome vesicle suspension. The crude cerasome vesicle suspension was ultrasonicated in a ultrasound bath for 10 min, then the suspension was further ultrasonicated for 5 min (amplitude 20, interval 3 s) with a probe-type ultrasonicator to obtain a stable system formed by the complete dispersion of cerasome vesicles, that is, a refined cerasome vesicle suspension. The unencapsulated rosuvastatin in the refined cerasome vesicle suspension was removed by a dialysis bag. Then the cerasome vesicle suspension was allowed to stand for at least 24 hours to promote the cerasome monomer molecules to form an inherently rigid inorganic polysiloxane network on the surface of the cerasome.

(2) Activation and Coupling of Hyaluronic Acid ("HA"):

1 g of HA (having a molecular weight of about 100 KDa) was completely dissolved in ultrapure water, and 0.1 g of 1-(3-dimethylaminopropyl)-3-ethylcarbodiimide hydrochloride (EDC·HCl) and 0.12 g of N-hydroxysulfosuccinimide (sulfo-NHS) coupling agent were added to activate the carboxyl group. After the solution was stirred at room temperature for 1 hour, acetone was added to precipitate the activated HA. The precipitation was filtered, washed with ethanol and dried in vacuo to give the activated HA. The same was formulated to a 0.1 mg mL$^{-1}$ aqueous solution, and 0.2 mL of the solution was transferred and dissolved in the cerasome vesicle suspension obtained in the above step (1), for coupling the activated carboxyl group in the activated HA to the amino group of the DSPE molecule incorporated in the lipid bilayer of the cerasome vesicle via forming amide bonds, to obtain three cerasome delivery systems HA-CL1@R, HA-CL2@R and HA-CL3@R, which were loaded with a therapeutic agent.

Figure 2:
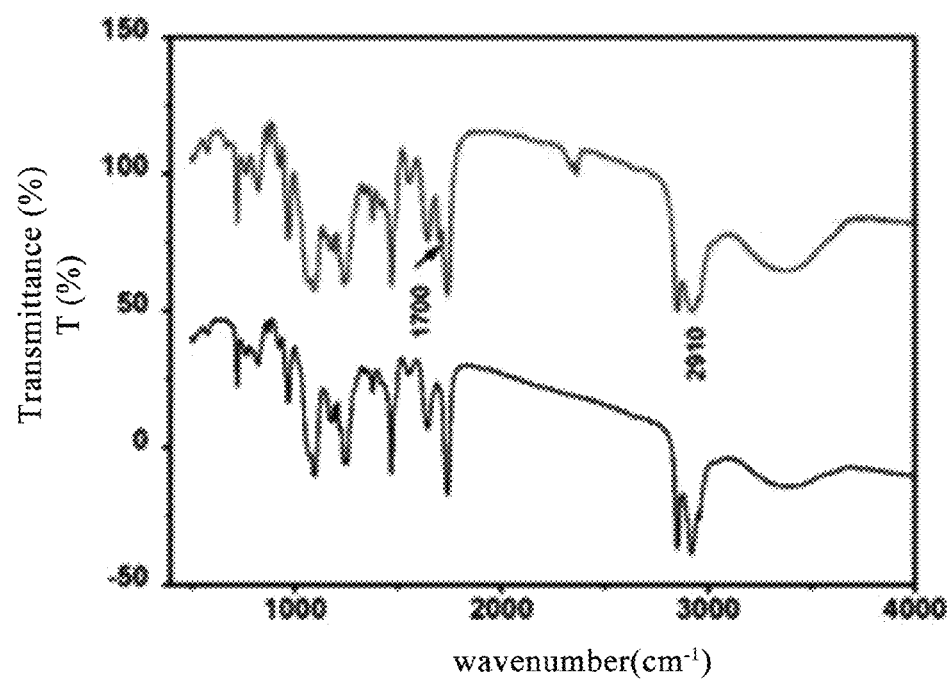
FIG. 2 shows the infrared spectrum of HA-CL1, including the infrared spectrum of CL1 loaded with rosuvastatin before (black, the lower line) and after (red, the upper line) binding to HA.

The coupling of HA to CL is confirmed by infrared characterization. The sample used for infrared characterization is a HA-CL1@R sample, which is loaded with rosuvastatin, and is prepared by the following steps: 6 mg of C1 and 1 mg of DSPE were weighed and dissolved with 10 mL of chloroform in a round bottom flask. The organic solvent was completely removed by means of rotary evaporation (55° C. water bath, 90 r/min, 30 min) to form a thin-film on the wall of the flask. 10 mL rosuvastatin aqueous solution was added (at a concentration of 2 mg/mL), and the flask was placed in a constant-temperature water bath kettle at 50° C. to fully hydrate the thin-film for 30 min. The same was ultrasonicated in a ultrasound bath for 10 min, and then further ultrasonicated for 5 min (amplitude 20, interval 3 s) with a probe-type ultrasonicator to obtain the cerasome vesicle. The cerasome vesicle was allowed to stand for at least 24 hours to promote the cerasome monomer molecules to form an inherently rigid inorganic polysiloxane network on the surface of the cerasome. 0.1 g of HA (having a molecular weight of about 100 KDa) was sufficiently dissolved in ultrapure water, 10 mg of EDC·HCl and 12 mg of sulfo-NHS coupling agent were added to activate the carboxyl group. After the solution was stirred at room temperature for 1 hour, acetone was added to precipitate the activated HA. The precipitation was filtered, washed with ethanol and dried in vacuo to give the activated HA. The same was formulated to a 0.1 mg mL$^{-1}$ aqueous solution, and 0.2 mL of the solution is transferred and dissolved in the cerasome vesicle suspension obtained in the above step (1), for coupling the activated carboxyl group in the activated HA and the amino group of the DSPE molecule incorporated in the lipid bilayer of the cerasome vesicle via forming amide bonds, to obtain a targeting cerasome HA-CL1@R1. After 24 hours from the start of the coupling reaction, HA-CL1@R was separated by high speed centrifugation at 12,000 rpm. The same was used for infrared spectra characterization after vacuum drying. As shown in FIG. 2, the absorption peak at 1100 nm demonstrates the presence of cerasome, and the absorption peaks at 1700 nm and 2910 nm indicate successful coupling of cerasome to HA.

2. Preparation of Cerasome Delivery Systems HA-CL1@LMHA, HA-CL2@LMHA and HA-CL3@LMHA which are Loaded with a Small-Molecular Hyaluronic Acid In this example, cerasome delivery systems HACL1@LMHA, HA-CL2@LMHA and HA-CL3@LMHA, which are loaded with a small-molecular hyaluronic acid, are prepared by the thin-film dispersion method. The surfaces of the cerasome vesicles of the above three cerasome delivery systems are partially modified by the targeting ligand hyaluronic acid (abbreviated as "HA") and are loaded with a small-molecular hyaluronic acid having a molecular weight of about 3411 Da (with a molecular formula of $(C_{14}H_{21}NO_{11})_n$, n=9, hereinafter represented by the abbreviation "LMHA"). The only difference is that the cerasome monomer molecules used in the preparation of the three cerasome delivery systems are the cerasome monomers C1, C2 and C3 as described in Example 1, respectively.

The specific preparation method for the HA-CL1@LMHA, HA-CL2@LMHA and HA-CL3@LMHA is the same as that for the cerasome delivery systems HA-CL1@R, HA-CL2@R and HA-CL3@R which are loaded with a therapeutic agent, as described in the above point 1, and the only differences are that in step (1), the 10 mL of rosuvastatin aqueous solution (at a concentration of 2 mg/mL) was replaced with 10 mL aqueous solution of a small-molecular hyaluronic acid having a molecular weight of 3411 Da (at a concentration of 0.5 mg/mL), and the unencapsulated small-molecular hyaluronic acid in the refined cerasome vesicle suspension was removed with a dialysis bag.

3. Preparation of Cerasome Delivery Systems HA-CL1@R+LMHA, HA-CL2@R+LMHA and HA-CL3@R+LMHA which are Loaded with a Therapeutic Agent and a Small-Molecular Hyaluronic Acid In this example, cerasome delivery systems HA-CL1@R+LMHA, HA-CL2@R+LMHA and HA-CL3@R+LMHA, which are loaded with a therapeutic agent, rosuvastatin, and a small-molecular hyaluronic acid concurrently, are prepared by the thin-film dispersion method. The surfaces of the cerasome vesicles of the above three cerasome delivery systems are partially modified by the targeting ligand hyaluronic acid (abbreviated as "HA"), and are loaded with a therapeutic agent, rosuvastatin (represented by the abbreviation "R") and a small-molecular hyaluronic acid having a molecular weight of about 3411 Da concurrently. The only difference is that the cerasome monomer molecules used in the preparation of the three cerasome delivery systems are the cerasome monomers C1, C2 and C3 as described in Example 1, respectively.

The specific preparation method for the HA-CL1@R+LMHA, HA-CL2@R+LMHA and HA-CL3@R+LMHA is substantially the same as the preparation method described in the above point 1 for the cerasome delivery systems HA-CL1@R, HA-CL2@R and HACL3@R which are loaded with a therapeutic agent. The only differences are that in step (1), the 10 mL of rosuvastatin aqueous solution (at a concentration of 2 mg/mL) was added simultaneously with 10 mL aqueous solution of a small-molecular hyaluronic acid having a molecular weight of 3411 Da (at a concentration of 0.5 mg/mL), and the unencapsulated rosuvastatin and small-molecular hyaluronic acid in the refined cerasome vesicle suspension were removed with a dialysis bag.

4. Preparation of Cerasome Delivery Systems HA-CL1@S, HA-CL2@S and HA-CL3@S which are Loaded with a CD44 Activator In this example, cerasome delivery systems HA-CL1@S, HA-CL2@S and HA-CL3@S, which are loaded with a CD44 activator, are prepared by the thin-film dispersion method. The surfaces of the cerasome vesicles of the above three cerasome delivery systems are partially modified by the targeting ligand hyaluronic acid (abbreviated as "HA"), and are loaded with a CD44 activator-CD44 antibody mAb (represented by the abbreviation "S"). The only difference is that the cerasome monomer molecules used in the preparation of the three cerasome delivery systems are the cerasome monomers C1, C2 and C3 as described in Example 1, respectively.

The specific preparation method for the HA-CL1@S, HA-CL2@S and HA-CL3@S is the same as the preparation method described in the above point 1 for the cerasome delivery systems HA-CL1@R, HA-CL2@R and HA-CL3@R which are loaded with a therapeutic agent. The only differences are that in step (1), the 10 mL of rosuvastatin aqueous solution (at a concentration of 2 mg/mL) was replaced with 10 mL of CD44 antibody mAb aqueous solution (at a concentration of 0.7 mg/mL), and the unencapsulated CD44 antibody mAb in the refined cerasome vesicle suspension was separated and removed with dextran gel column G-100.

Similarly, the preparation can also be carried out using CD44 activator LPS, and similar results were obtained.

5. Preparation of Cerasome Delivery Systems HA-CL1@R+S, HA-CL2@R+S and HA-CL3@R+S which are Loaded with a Therapeutic Agent and a CD44 Activator In this example, cerasome delivery systems HA-CL1@R+S, HA-CL2@R+S and HA-CL3@R+S, which are loaded with a therapeutic agent and a CD44 activator, are prepared by the thin-film dispersion method. The surfaces of the cerasome vesicles of the above three cerasome delivery systems are partially modified by the targeting ligand hyaluronic acid (abbreviated as "HA"), and are loaded with a therapeutic agent, rosuvastatin (represented by the abbreviation "R") and a CD44 activator-CD44 antibody mAb (represented by the abbreviation "S") concurrently. The only difference is that the cerasome monomer molecules used in the preparation of the three cerasome delivery systems are the cerasome monomers C1, C2 and C3 as described in Example 1, respectively.

The specific preparation method for the HA-CL1@R+S, HA-CL2@R+S and HA-CL3@R+S is substantially the same as the preparation method described in the above point 1 for the cerasome delivery systems HA-CL1@R, HA-CL2@R and HA-CL3@R which are loaded with a therapeutic agent. The only differences are that in step (1), the 10 mL of rosuvastatin aqueous solution (at a concentration of 2 mg/mL) was used with 10 mL of CD44 antibody mAb aqueous solution (at a concentration of 0.7 mg/mL) concurrently, and the unencapsulated rosuvastatin and CD44 antibody mAb in the refined cerasome vesicle suspension were removed with dextran gel column G-100.

Similarly, the preparation can also be carried out using the CD44 activator LPS, and similar results were obtained.

6. Preparation of Cerasome Delivery Systems HA-CL1@T, HA-CL2@T and HA-CL3@T which are Loaded with a Tracer In this example, cerasome delivery systems HA-CL1@T, HA-CL2@T and HA-CL3@T, which are loaded with a tracer, are prepared by the thin-film dispersion method. The surfaces of the cerasome vesicles of the above three cerasome delivery systems are partially modified by the targeting ligand hyaluronic acid (abbreviated as "HA"), and are loaded with an MRI tracer gadopentetic acid (represented by the abbreviation "T"). The only difference is that the cerasome monomer molecules used in the preparation of the three cerasome delivery systems are the cerasome monomers C1, C2 and C3 as described in Example 1, respectively.

The specific preparation method for the HA-CL1@T, HA-CL2@T and HA-CL3@T is the same as the preparation method described in the above point 1 for the cerasome delivery systems HA-CL1@R, HA-CL2@R and HA-CL3@R which are loaded with a therapeutic agent. The only differences are that in step (1), the 10 mL of rosuvastatin aqueous solution (at a concentration of 2 mg/mL) was replaced with 10 mL of gadopentetic acid aqueous solution (at a concentration of 3 mg/mL), and the unencapsulated gadopentetic acid in the refined cerasome vesicle suspension was removed with a dialysis bag.

Similarly, the preparation can also be carried out using the tracer gadoterate meglumine or gadodiamide, and similar results were obtained.

7a. Preparation of Cerasome Delivery Systems HA-CL1@AuNPs, HA-CL2@AuNPs and HA-CL3@AuNPs which are Loaded with a Tracer In this example, cerasome delivery systems HA-CL1@AuNPs, HA-CL2@AuNPs and HA-CL3@AuNPs, which are loaded with a tracer, are prepared by the thin-film dispersion method. The surfaces of the cerasome vesicles of the above three cerasome delivery systems are partially modified by the targeting ligand hyaluronic acid (abbreviated as "HA"), and are loaded with a CT tracer, nanogold (represented by the abbreviation "AuNPs"). The only difference is that the cerasome monomer molecules used in the preparation of the three cerasome delivery systems are the cerasome monomers C1, C2 and C3 as described in Example 1, respectively.

The specific preparation method for the HA-CL1@AuNPs, HA-CL2@AuNPs and HA-CL3@AuNPs is the same as the preparation method described in the above point 1 for the cerasome delivery systems HA-CL1@R, HA-CL2@R and HA-CL3@R which are loaded with a therapeutic agent. The only differences are that in step (1), the 10 mL of rosuvastatin aqueous solution (at a concentration of 2 mg/mL) was replaced with 10 mL of nanogold solution (at a concentration of 1 mg/mL), and the unencapsulated nanogold in the refined cerasome vesicle suspension was removed with dextran gel column G-100.

7b. Preparation of Cerasome Delivery Systems HA-CL1@Iodixanol, HA-CL2@Iodixanol and HA-CL3@Iodianol which are Loaded with a Tracer In this example, cerasome delivery systems HA-CL1@I, HA-CL2@I and HA-CL3@I, which are loaded with a tracer, are prepared by the thin-film dispersion method.

The surfaces of the cerasome vesicles of the above three cerasome delivery systems are partially modified by the targeting ligand hyaluronic acid (abbreviated as "HA"), and are loaded with a CT tracer, iodixanol or iopromide (represented by the abbreviation "I"). The only difference is that the cerasome monomer molecules used in the preparation of the three cerasome delivery systems are the cerasome monomers C1, C2 and C3 as described in Example 1, respectively.

The specific preparation method for the HA-CL1@I, HA-CL2@I and HA-CL3@I is the same as the preparation method described in the above point 1 for the cerasome delivery systems HA-CL1@R, HA-CL2@R and HA-CL3@R which are loaded with a therapeutic agent. The only differences are that in step (1), the 10 mL of rosuvastatin aqueous solution (at a concentration of 2 mg/mL) was replaced with 10 mL of iodixanol or iopromide solution (at a concentration of 1 μg/mL), and the unencapsulated iodixanol or iopromide in the refined cerasome vesicle suspension was removed with dextran gel column.

8a. Preparation of Cerasome Delivery Systems HA-CL1@AuNPs+S, HA-CL2@AuNPs+S and HA-CL3@AuNPs+S which are Loaded with a Tracer and a CD44 Activator In this example, cerasome delivery systems HA-CL1@AuNPs+S, HA-CL2@AuNPs+S and HA-CL3@AuNPs+S, which are loaded with a tracer and a CD44 activator concurrently, are prepared by the thin-film dispersion method. The surfaces of the cerasome vesicles of the above three cerasome delivery systems are partially modified by the targeting ligand hyaluronic acid (abbreviated as "HA"), and are loaded with a CT tracer, nanogold (represented by the abbreviation "AuNPs") and a CD44 activator-CD44 antibody mAb (represented by the abbreviation "S") concurrently. The only difference is that the cerasome monomer molecules used in the preparation of the three cerasome delivery systems are the cerasome monomers C1, C2 and C3 as described in Example 1, respectively.

The specific preparation method for the HA-CL1@AuNPS+S, HA-CL2@AuNPS+S and HA-CL3@AuNPS+S is substantially the same as the preparation method described in the above point 1 for the cerasome delivery systems HA-CL1@R, HA-CL2@R and HACL3@R which are loaded with a therapeutic agent. The only differences are that in step (1), the 10 mL of nanogold solution (at a concentration of 1 mg/mL) was used with 10 mL of an CD44 antibody mAb aqueous solution (at a concentration of 0.7 mg/mL) concurrently, and the unencapsulated nanogold and CD44 antibody mAb in the refined cerasome vesicle suspension were removed with dextran gel column G-100.

8b. Preparation of Cerasome Delivery Systems HA-CL1@I+S, HA-CL2@I+S and HA-CL3@I+S which are Loaded with a Tracer and a CD44 Activator In this example, cerasome delivery systems HA-CL1@I+S, HA-CL2@I+S and HA-CL3@I+S, which are loaded with a tracer and a CD44 activator concurrently, are prepared by the thin-film dispersion method. The surfaces of the cerasome vesicles of the above three cerasome delivery systems are partially modified by the targeting ligand hyaluronic acid (abbreviated as "HA"), and are loaded with a CT tracer, iodixanol or iopromide (represented by the abbreviation "I") and a CD44 activator-LPS (represented by the abbreviation "S") concurrently. The only difference is that the cerasome monomer molecules used in the preparation of the three cerasome delivery systems are the cerasome monomers C1, C2 and C3 as described in Example 1, respectively.

The specific preparation method for the HA-CL1@I+S, HA-CL2@I+S and HA-CL3@I+S is substantially the same as the preparation method described in the above point 1 for the cerasome delivery systems HA-CL1@R, HA-CL2@R and HA-CL3@R which are loaded with a therapeutic agent. The only differences are that in step (1), the 10 mL of iodixanol or iopromide aqueous solution (at a concentration of 1 μg/mL) was used with the 10 mL of LPS aqueous solution (at a concentration of 0.7 mg/mL) concurrently, and the unencapsulated iodixanol or iopromide and LPS in the refined cerasome vesicle suspension were removed with dextran gel column G-200.

9. Preparation of Cerasome Delivery Systems HA-CL1@R+LMHA+T+S, HA-CL2@R+LMHA+T+S and HA-CL3@R+LMHA+T+S which are Loaded with a Therapeutic Agent, a Small-Molecular Hyaluronic Acid, a Tracer and a CD44 Activator In this example, cerasome delivery systems HA-CL1@R+LMHA+T+S, HA-CL2@R+LMHA+T+S and HA-CL3@R+LMHA+T+S, which are loaded with a therapeutic agent, rosuvastatin, a small-molecular hyaluronic acid, a tracer gadopentetic acid and a CD44 activator concurrently, are prepared by the thin-film dispersion method. The surfaces of the cerasome vesicles of the above three cerasome delivery systems are partially modified by the targeting ligand hyaluronic acid (abbreviated as "HA"), and are loaded with a therapeutic agent, rosuvastatin (represented by the abbreviation "R"), a small-molecular hyaluronic acid having a molecular weight of about 3411 Da, an MRI tracer gadopentetic acid (represented by the abbreviation "T") and a CD44 activator—CD44 antibody mAb (represented by the abbreviation "S") concurrently. The only difference is that the cerasome monomer molecules used in the preparation of the three cerasome delivery systems are the cerasome monomers C1, C2 and C3 as described in Example 1, respectively.

The specific preparation method for the HA-CL1@R+LMHA+T+S, HA-CL2@R+LMHA+T+S and HA-CL3@R+LMHA+T+S is substantially the same as the preparation method described in the above point 1 for the cerasome delivery systems HA-CL1@R, HA-CL2@R and HA-CL3@R which are loaded with a therapeutic agent. The only differences are that in step (1), the 10 mL of rosuvastatin aqueous solution (at a concentration of 2 mg/mL), the 10 mL aqueous solution of small-molecular hyaluronic acid having a molecular weight of 3411 Da (at a concentration of 0.5 mg/mL), the 10 mL of gadopentetic acid aqueous solution (at a concentration of 3.0 mg/mL), and the 10 mL of CD44 antibody mAb aqueous solution (at a concentration of 0.7 mg/mL) were used concurrently, and the unencapsulated rosuvastatin, small-molecular hyaluronic acid, gadopentetic acid and CD44 antibody mAb in the refined cerasome vesicle suspension were removed with dextran gel column G-100.

Similarly, the preparation can also be carried out using the CD44 activator LPS, and the tracer gadoterate meglumine, and similar results were obtained.

10. Preparation of Blank Cerasome Delivery Systems HA-CL1, HA-CL2, and HA-CL3 (as Comparative Examples)

In this example, blank cerasome delivery systems HA-CL1, HA-CL2, and HA-CL3 are prepared by the thin-film dispersion method. The surfaces of the cerasome vesicles of the above three cerasome delivery systems are partially modified by the targeting ligand hyaluronic acid (abbreviated as "HA") but are not loaded with any substance for diagnosing, preventing, and/or treating the vulnerable plaque or a disease associated with the vulnerable plaque, and the only difference is that the cerasome monomer molecules used in the preparation of the three cerasome delivery systems are the cerasome monomers C1, C2 and C3 as described in Example 1, respectively.

The specific preparation method for the HA-CL1, HA-CL2, and HA-CL3 is substantially the same as the preparation method described in the above point 1 for the cerasome delivery systems HA-CL1@R, HA-CL2@R and HA-CL3@R which are loaded with a therapeutic agent. The only differences are that in step (1), the 10 mL of rosuvastatin aqueous solution (at a concentration of 2 mg/mL) was replaced with pure water and the step of removing unencapsulated material by means of dialysis was omitted.

11. Preparation of Non-Targeting Cerasome Delivery Systems CL1@R, CL2@R and CL3@R which are Loaded with a Therapeutic Agent (as Comparative Examples)

In this example, non-targeting cerasome delivery systems CL1@R, CL2@R and CL3@R, which are loaded with a therapeutic agent, are prepared by the thin-film dispersion method. The surfaces of the cerasome vesicles of the above three cerasome delivery systems are not modified by the targeting ligand hyaluronic acid (abbreviated as "HA") but are loaded with rosuvastatin (represented by the abbreviation "R"), a substance for the prevention and/or treatment of the vulnerable plaque or a disease associated with the vulnerable plaque. The only difference is that the cerasome monomer molecules used in the preparation of the three cerasome delivery systems are the cerasome monomers C1, C2 and C3 as described in Example 1, respectively.

The specific preparation method for the CL1@R, CL2@R and CL3@R is substantially the same as the preparation method described in the above point 1 for the cerasome delivery systems HA-CL1@R, HA-CL2@R and HA-CL3@R which are loaded with a therapeutic agent. The only difference is that step (2) was omitted.

12a. Preparation of Non-Targeting Cerasome Delivery Systems CL1@AuNPs, CL2@AuNPs and CL3@AuNPs which are Loaded with a Tracer (as Comparative Examples)

In this example, non-targeting cerasome delivery systems CL1@AuNPS, CL2@AuNPS and CL3@AuNPS, which are loaded with a tracer, are prepared by the thin-film dispersion method. The surfaces of the cerasome vesicles of the above three cerasome delivery systems are not modified by the targeting ligand hyaluronic acid (abbreviated as "HA"), but are loaded with a CT tracer, nanogold (represented by the abbreviation "AuNPs"). The only difference is that the cerasome monomer molecules used in the preparation of the three cerasome delivery systems are the cerasome monomers C1, C2 and C3 as described in Example 1, respectively.

The specific preparation method for the CL1@AuNPS, CL2@AuNPS and CL3@AuNPS is substantially the same as the preparation method described in the above point 7 for the cerasome delivery systems HA-CL1@AuNPs, HA-CL2@AuNPs and HA-CL3@AuNPs which are loaded with a tracer. The only difference is that step (2) was omitted.

12b. Preparation of Non-Targeting Cerasome Delivery Systems CL1@1, CL2@I and CL3@I which are Loaded with a Tracer (as Comparative Examples)

In this example, non-targeting cerasome delivery systems CL1@I, CL2@I and CL3@I, which are loaded with a tracer, are prepared by the thin-film dispersion method. The surfaces of the cerasome vesicles of the above three cerasome delivery systems are not modified by the targeting ligand hyaluronic acid (abbreviated as "HA"), but are loaded with a CT tracer, iodixanol (represented by the abbreviation "I"). The only difference is that the cerasome monomer molecules used in the preparation of the three cerasome delivery systems are the cerasome monomers C1, C2 and C3 as described in Example 1, respectively.

The specific preparation method for the CL1@I, CL2@I and CL3@I is substantially the same as the preparation method described in the above point 7 for the cerasome delivery systems HA-CL1@I, HA-CL2@I and HA-CL3@I which are loaded with a tracer. The only difference is that step (2) was omitted.

13. Preparation of Liposome Delivery System HA-PL@R which is Loaded with a Therapeutic Agent (as a Comparative Example)

In this example, liposome delivery system HA-PL@R, which is loaded with a therapeutic agent, is prepared by the thin-film dispersion method. The surface of the liposome vesicle of the liposome delivery system HA-PL@R is partially modified by the targeting ligand hyaluronic acid (abbreviated as "HA") and is loaded with rosuvastatin (represented by the abbreviation "R"), a substance for the prevention and/or treatment of the vulnerable plaque or a disease associated with the vulnerable plaque.

The specific preparation method for HA-PL@R is as follows:

(1) Preparation of Liposome Vesicle Suspension:

4 mg of distearoylphosphatidylcholine (DSPC), 1 mg of cholesterol and 1 mg of distearylphosphatidylethanolamine (DSPE) (with a mass ratio of 4:1:1) was weighed and dissolved with 10 mL of chloroform. The organic solvent was removed by means of slow rotary evaporation (65° C. water bath, 90 r/min, 30 min) to form a thin-film on the wall of the flask. 10 mL of rosuvastatin aqueous solution (at a concentration of 2.0 mg/mL) was added to the round bottom flask, and the flask was placed in a constant-temperature water bath kettle at 50° C. to fully hydrate the thin-film, so as to form the crude liposome vesicle suspension. The crude liposome vesicle suspension was ultrasonicataed in the ultrasound bath, and the same was finally ultrasonicated for 3 min (amplitude 20, interval 3 s) with a probe-type ultrasonicator to obtain a disperse system formed by the completely dispersion of liposome vesicles, that is, the refined liposome vesicle suspension. The unencapsulated rosuvastatin in the refined liposome vesicle suspension was removed with a dialysis bag.

(2) Activation and Coupling of Hyaluronic Acid ("HA"):

1 g of HA (having a molecular weight of about 100 KDa) was completely dissolved in ultrapure water, and 0.1 g of 1-(3-dimethylaminopropyl)-3-ethylcarbodiimide hydrochloride (EDC·HCl) and 0.12 g of N-hydroxysulfosuccinimide (sulfo-NHS) coupling agent were added to activate the carboxyl group. After the solution was stirred at room temperature for 1 hour, anhydrous ethanol was added to precipitate the activated HA. The precipitation was filtered, washed with ethanol and dried in vacuo to give the activated HA. The same was formulated to 0.1 mg mL$^{-1}$ aqueous solution, and 0.2 mL of the solution was transferred and dissolved in the liposome vesicle suspension obtained in the above step (1), for coupling the activated carboxyl group in the activated HA to the amino group of the DSPE molecule incorporated in the lipid bilayer of the liposome vesicle via forming amide bonds, to obtain the liposome delivery system HA-PL@R loaded with a therapeutic agent.

14a. Preparation of Liposome Delivery System HA-PL@T which is Loaded with a Tracer (as a Comparative Example)

In this example, liposome delivery system HA-PL@T, which is loaded with a tracer, is prepared by the thin-film dispersion method. The surface of the liposome vesicle of the liposome delivery system HA-PL@T is partially modified by the targeting ligand hyaluronic acid (abbreviated as "HA"), and is loaded with an MRI tracer, gadopentetic acid (represented by the abbreviation "T").

The specific preparation method for the HA-PL@T is substantially the same as the preparation method described in the above point 13 for the liposome delivery systems HA-PL@R which is loaded with a therapeutic agent. The only differences are that in step (1), the 10 mL of rosuvastatin aqueous solution (at a concentration of 2.0 mg/mL) was replaced with 10 mL of gadopentetic acid (as a tracer) aqueous solution (at a concentration of 3.0 mg/mL), and the unencapsulated gadopentetic acid (as a tracer) in the refined liposome vesicle suspension was removed with dialysis bag.

Similarly, the preparation can also be carried out using the tracer gadoterate meglumine, and similar results were obtained.

Example 3: Investigation of Properties of Cerasome Delivery System of the Present Disclosure In this example, the cerasome delivery systems loaded with the therapeutic agent, HA-CL1@R, HA-CL2@R and HA-CL3@R, which are prepared in Example 2, are taken as examples to prove that the cerasome delivery system of the present disclosure has stable and controllable properties and is therefore suitable for the diagnosis, prevention and treatment of the vulnerable plaque or a disease associated with the vulnerable plaque. Meanwhile, for the convenience of comparison, a liposome delivery system loaded with the therapeutic agent, HA-PL@R (as a comparative example), which is-prepared in Example 2, is also used in the present example.

1. Method for the Determination of Drug Concentration:

Rosuvastatin has a strong ultraviolet absorption property, and thus its content can be determined with the HPLC-UV method (using Waters 2487, Waters Corporation, U.S.A.) by using with the ultraviolet absorption property of rosuvastatin. A standard quantitative equation was established with various concentrations of rosuvastatin solution (X) versus the peak area of the HPLC chromatographic peak (Y).

2. Determination of Hydrodynamic Size:

The hydrodynamic sizes of the cerasome delivery systems HA-CL1@R, HA-CL2@R and HA-CL3@R of the present disclosure and the liposome delivery system HA-PL@R as a comparative example were measured by a laser particle analyzer (BI-Zeta Plus/90 Plus, Brookhaven Instruments Corporation, U.S.A.), and the specific results are shown in Table 1.

3. Determination of Encapsulation Rate:

1.0 mL of cerasome vesicle suspension was taken, and the suspension was allowed to form a strong acidic environment by adding excess amount of HCl. The suspension was further ultrasonicated to accelerate the release of the drug from the cerasome vesicle. The drug content in the resulting liquid was measured by HPLC (Waters 2487, Waters Corporation, U.S.A.), and the encapsulation rate was calculated in accordance with Equation 1.

$$\text{Encapsulation rate } (\%) = \frac{M_{encapsulated\ drug\ amount}}{M_{added\ drug\ amount}} \times 100\% \qquad \text{Equation 1}$$

4. Determination of Drug-Loading Rate:

The method for determining the drug-loading rate is similar to that for determining the encapsulation rate, except that the calculation method is slightly different. Cerasome vesicle suspension was taken, and the suspension was allowed to form a strong acidic environment by adding excess amount of HCl. The suspension was further ultrasonicated to accelerate the release of the drug from the cerasome vesicle. The drug content in the resulting liquid was measured by HPLC (Waters 2487, Waters Corporation, U.S.A.), and the drug-loading rate was calculated in accordance with Equation 2.

$$\text{Drug-loading rate } (\%) = \frac{M_{encapsulated\ drug\ amount}}{M_{added\ lipid\ mass}} \times 100\% \qquad \text{Equation 2}$$

TABLE 1

List of various properties

| Name | Hydrodynamic Size (nm) | Drug Encapsulation rate (%) | Drug-loading rate (%) | Surface potential (mV) |
|---|---|---|---|---|
| HA-CL1@R | 210 ± 12 | 85.5 ± 4.7 | 4.96 ± 0.34 | −2.9 ± 1.8 |
| HA-CL2@R | 202 ± 18 | 84.3 ± 4.2 | 4.93 ± 0.34 | −31.6 ± 1.2 |
| HA-CL3@R | 193 ± 16 | 81.7 ± 3.8 | 4.93 ± 0.34 | −33.2 ± 1.5 |
| HA-PL@R | 183 ± 13 | 83.8 ± 5.3 | 4.93 ± 0.34 | −26.3 ± 1.7 |

Note:
The above data are expressed in the form of "average + standard deviation" of the results of 5 determinations in parallel.

5. Investigation of Long-Term Stability

Figure 3:
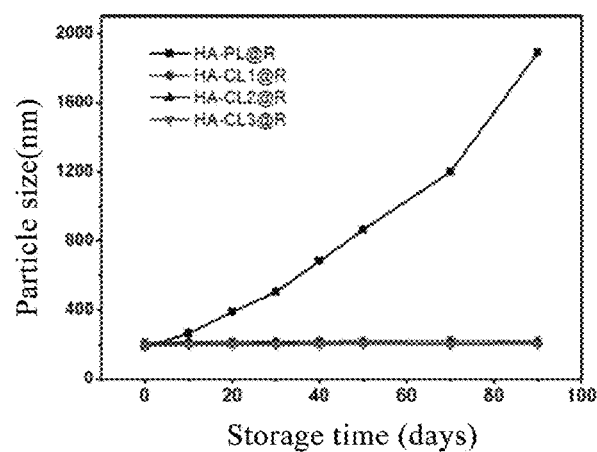
FIG. 3 is a graph showing the change in particle size of the cerasome delivery system of the present disclosure and the liposome delivery system as a control after being stored at 4° C. for 90 days.

The cerasome delivery systems HA-CL1@R, HA-CL2@R and HA-CL3@R of the present disclosure and the liposome delivery system HA-PL@R as a control were stored at 4° C., and sampled at different time points. The changes in the hydrodynamic sizes thereof were detected by a laser particle analyzer (BI-Zeta Plus/90 Plus, Brookhaven Instruments Corporation, U.S.A.), and the results are shown in FIG. 3. It can be seen that the particle size of the liposome delivery system HA-PL@R is significantly increased with the storage time. This is very likely due to the fact that the liposome vesicles are not stable, and easily aggregated or fused. Moreover, due to the poor stability, liposome vesicles are easily cleared by the reticuloendothelial system in the body, resulting in a short half-life and limitations when applied to humans.

In contrast, the average hydrodynamic sizes of HA-CL1@R, HA-CL2@R, and HA-CL3@R remain almost unchanged after 90 days of storage, and no delamination, flocculation or other similar phenomenon is observed throughout the test period. The average hydrodynamic size of HA-PL@R increases from 183 nm to about 2 μm, and from the appearance, obvious precipitation appears after 10 days of storage. After 90 days of storage, HA-PL@R is in the form of flocculent precipitation, unable to re-disperse. It can be seen that the cerasome delivery systems of the present disclosure, HA-CL1@R, HA-CL2@R and HA-CL3@R, have better storage stability than the liposome delivery system HA-PL@R. Thus, they have potential for application as a long-circulating, targeted drug delivery system.

6. Investigation of Long-Term Encapsulation Rate

Figure 4:
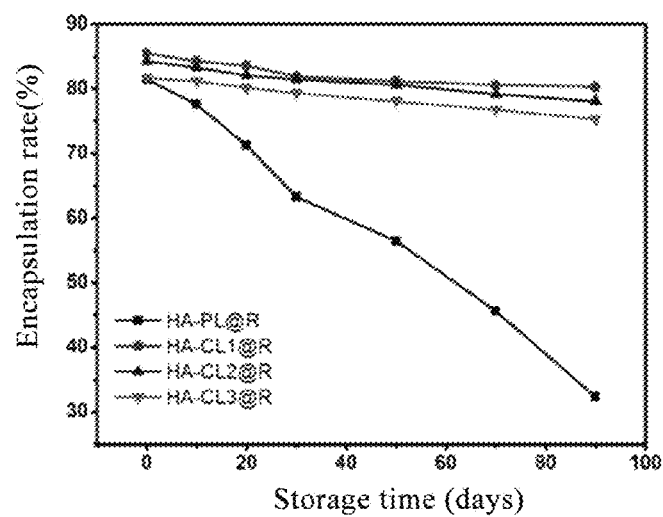
FIG. 4 is a graph showing the change in the encapsulation rate of the drug of the cerasome delivery system of the present disclosure and the liposome delivery system as a control after being stored at 4° C. for 90 days.

The cerasome delivery systems HA-CL1@R, HA-CL2@R and HA-CL3@R of the present disclosure and the liposome delivery system HA-PL@R as a control were stored at 4° C., and sampled at different time points, and the free drug was removed by ultrafiltration and centrifugation to detect changes in the encapsulation rate thereof, and the results are shown in FIG. 4.

As shown in the figure, there is no significant change in the drug content in the cerasome delivery systems HA-CL1@R, HA-CL2@R and HA-CL3@R after 90 days of standing. In contrast, the drug content in the liposome delivery system HA-PL@R drops dramatically to around 30%. This indicates that the release rate of the encapsulated drug is closely related to the nature of the lipid bilayer. The inorganic polysiloxane network on the surface of the cerasome vesicle effectively protects the internal lipid bilayer structure and decreases the permeability of the lipid bilayer, so that the drug is not easily leaked. In contrast, liposome vesicles have poor stability due to lack of the protective effect of inorganic polysiloxane network on their surface, so that the drug is easily leaked.

The data above clearly demonstrates that the long-term storage stability of the cerasome delivery system of the present disclosure is excellent, and the particle size does not change much after storage for three months at 4° C. with low leakage rate of the drug.

7. Study on In Vitro Drug Release Performance 2 mL of the cerasome delivery system of the present disclosure HA-CL1@R and 2 mL of the liposome delivery system HAPL@R as a control were placed in a dialysis bag and sealed. The dialysis bag was then placed in 50 mL of release medium (PBS solution, pH=7.4) and incubated at 37° C. for 120 h. 2 mL of the release liquid was taken at different time points and the same volume of PBS solution was replenished. The drug content in the release liquid was detected by HPLC (Waters 2487, Waters Corporation, U.S.A.), and the cumulative drug release rate was calculated according to Equation 3.

$$CRP\ (\%) = \frac{V_r \sum_{1}^{n-1} C_i + V_0 C_n}{M_{drug}} \times 100\%$$ Equation 3

The meaning of each parameter in Equation 3 is as follows:

CRP: cumulative drug release rate

Ve: displacement volume of the release liquid, Ve being 2 mL herein

V0: volume of the release liquid in the release system, V0 being 50 mL herein $C_i$: concentration of drug in the release liquid at the $i^{th}$ replacement and sampling, in μg/mL M Drug: total mass of drug in the cerasome or liposome delivery system, in μg n: number of times for replacement of the release liquid $C_n$: drug concentration in the release system measured after the $n^{th}$ replacement of the release liquid.

Figure 5:
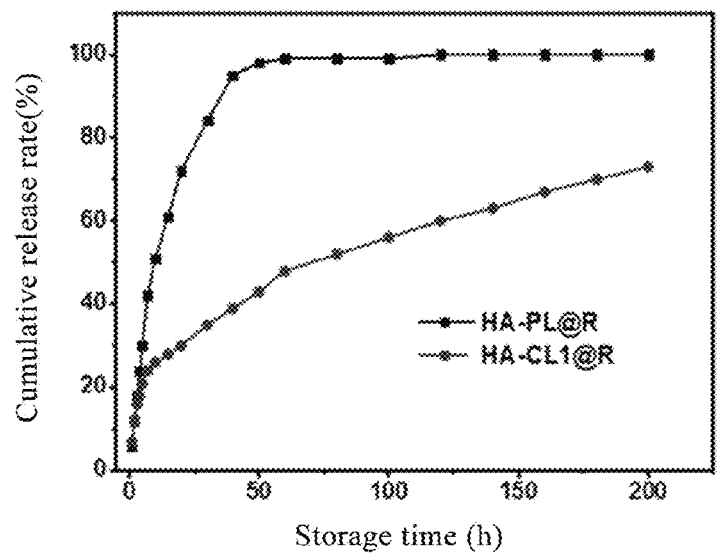
FIG. 5 is a graph showing the change in cumulative drug release rate of the cerasome delivery system of the present disclosure and the liposome delivery system as a control.

In vitro release is an important index for evaluating the nanoparticle delivery systems. FIG. 5 is a graph showing the change in cumulative drug release rate of the cerasome delivery system of the present disclosure HA-CL1@R and the liposome delivery system HA-PL@R as a control. As shown in the figure, the liposome delivery system HA-PL@R almost releases 100% of the drug within 30 h. The cerasome delivery system HA-CL1@R releases faster in the first 3 hours, about 15% within 3 hours. After that, the drug release rate gradually slows down, and only 59.5% of the drug is released after 120 hours. The faster drug release rate in the early stage may be caused by the release behavior of a drug that is partially adsorbed or precipitated on the surface of the cerasome vesicle which can be rapidly dissolved and diffused into the release medium. The drug release in the later stage is mainly the release of the drug encapsulated in the cerasome vesicle, which is characterized by sustained and slow release behavior. The results of the in vitro release test show that the release of the drug from the cerasome vesicle can be effectively retarded because the surface of the cerasome vesicle is covered by the inorganic polysiloxane network, and the void between the lipid bilayers is reduced, and thus the density of the lipid bilayer is increased. The results of the in vitro release test indicate that cerasome vesicles as drug carriers have slow and sustained release properties.

Figure 6:
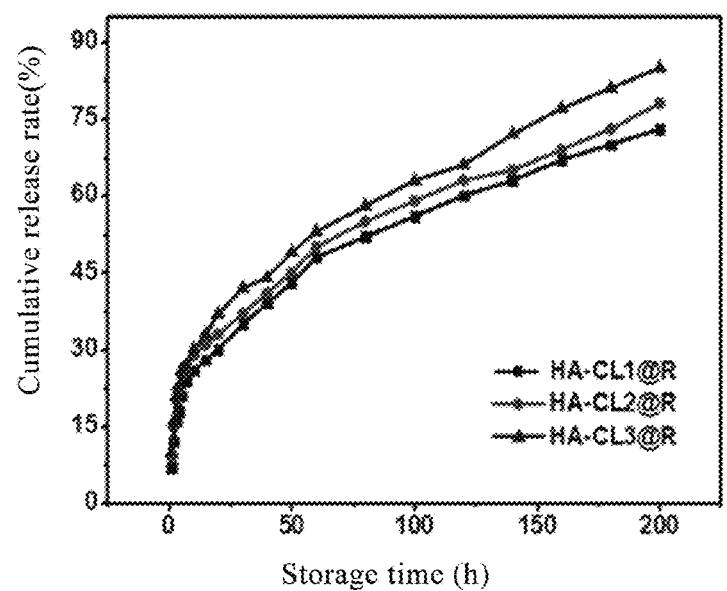
FIG. 6 is a graph showing the change in cumulative drug release rate for three cerasome delivery system of the present disclosure.

In addition, similar studies have found that the in vitro drug release properties of the cerasome delivery systems of the present disclosure HA-CL1@R, HA-CL2@R and HA-CL3@R are similar, wherein HA-CL3@R has the fastest drug release speed (see FIG. 6). This indicates that the three cerasome delivery systems of the present disclosure HA-CL1@R, HA-CL2@R and HA-CL3@R have similar drug release mechanisms and properties.

Example 4: Study on In Vivo Release Stability of Cerasome Delivery System of the Present Disclosure In this example, the cerasome delivery systems, HA-CL1@R and HA-CL2@R which are loaded with rosuvastatin and prepared in Example 2, are used as an example to prove that the cerasome delivery system of the present disclosure is capable of remaining relatively stable at vulnerable plaques as compared to liposome delivery systems, thereby achieving the effect of sustained release of the drug over a prolonged period of time. Meanwhile, for convenience of comparison, the liposome delivery system, HA-PL@R which is loaded with rosuvastatin and prepared in Example 2, is also used in this example as a comparative example.

Figure 7:
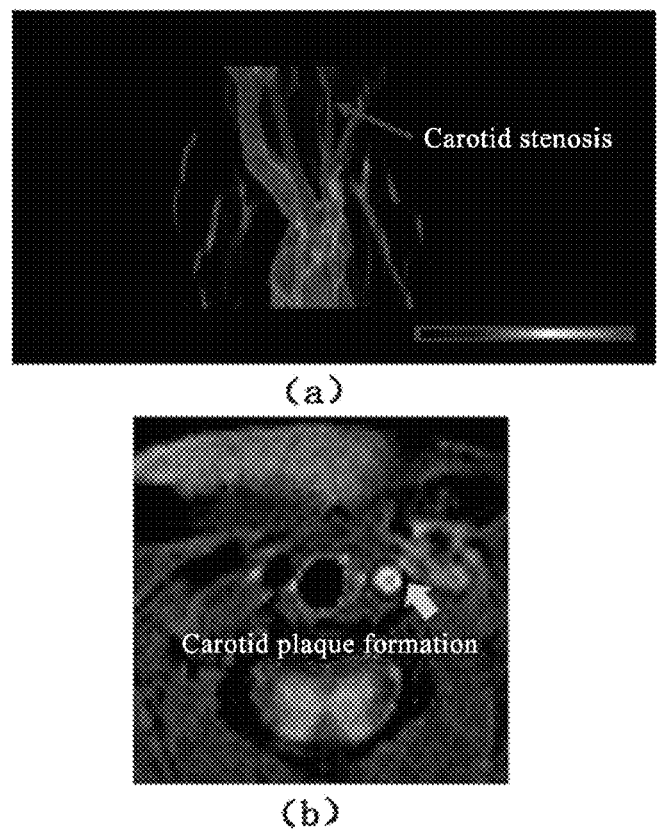
FIG. 7 shows images of the nuclear magnetic resonance imaging of a mouse atherosclerotic vulnerable plaque model constructed in Example 4.

Experimental Method:

SPF-grade ApoE−/− mice (18 mice, 10 weeks old, weight 20 f 1 g) are taken as experimental animals. The mice were fed with an adaptive high-fat diet (fat 10% (w/w), cholesterol 2% (w/w), sodium cholate 0.5% (w/w), and the rest being normal feed for mice) for 4 weeks, and then anaesthetized by intraperitoneal injection of 1% sodium pentobarbital (prepared by adding 1 mg of sodium pentobarbital to 100 ml of normal saline) at a dose of 40 mg/kg. Then, the mice were fixed on the surgical plate in the supine position, disinfected around the neck with 75% (v/v) alcohol, the neck skin was cut longitudinally, the anterior cervical gland was bluntly separated, and the beating left common carotid artery can be observed on the left side of the trachea. The common carotid artery was carefully separate to the bifurcation. A silicone cannula with a length of 2.5 mm and an inner size of 0.3 mm was placed on the outer periphery of the left common carotid artery. The proximal and distal segments of the cannula were narrowed and fixed by filaments. Local tightening causes rapid blood flow in the proximal end with increased shear force, and thus damage to the intima of the blood vessel. The carotid artery was repositioned and the neck skin was intermittently sutured. All operations were performed under a 10×stereomicroscope. After awakened from the surgery, the mice were returned to the cage, where the ambient temperature was maintained at 20-25° C., and the light was kept under a 12 h/12 h light/dark cycle. At the 4th week after the surgery, lipopolysaccharide (LPS) (1 mg/kg in 0.2 ml phosphate buffered saline, Sigma, U.S.A.) was injected intraperitoneally twice a week for 10 weeks to induce chronic inflammation. At the 8th week after the surgery, mice were placed in a 50 ml syringe (sufficient vents reserved) to trigger restrictive mental stress, 6 hours/day, 5 days per week for a total of 6 weeks. The mouse model of atherosclerotic vulnerable plaque was completed at the 14th week after the surgery. FIGS. 7(a) and 7(b) show images of the nuclear magnetic resonance imaging of the mouse atherosclerotic vulnerable plaque model. It can be seen from the part at which the arrow points that the left carotid plaque has been formed, suggesting successful modeling, and the right carotid can be used as a normal arterial vessel wall for comparison.

The mice were randomly divided into three groups with 6 mice per group, depending on the targeted delivery system used, i.e., the cerasome delivery system group 1 (using the cerasome delivery system, HA-CL1@R loaded with rosuvastatin and prepared in Example 2), the cerasome delivery system group 2 (using the cerasome delivery system, HA-CL2@R loaded with rosuvastatin and prepared in Example 2) and the liposome delivery system group (using the liposome delivery system, HA-PL@R loaded with rosuvastatin and prepared in Example 2, as a comparative example).

On the day of the experiment, HA-CL1@R, HA-CL2@R and HA-PL@R were administered via intravenous injection at a single dose of 5 mg of rosuvastatin per kg body weight for the above three groups of mice, respectively. The percentage of drug exposure at the arterial vulnerable plaque (which reflects changes in the concentration of rosuvastatin at the vulnerable plaque after injection of the experimental drug over time) was determined by liquid chromatography-mass spectrometry:

(1) Preparation of Standard Solution 0.0141 g of rosuvastatin was accurately weighed, placed in a 25 mL volumetric flask, dissolved with methanol and diluted to the mark, shaken and formulated as a stock solution of rosuvastatin reference substance at a concentration of 56.4 μg/mL. The stock solution of rosuvastatin reference substance was diluted with methanol to a series of standard solutions of 10, 1, 0.5, 0.125, 0.05, 0.025, 0.01, 0.002, 0.0004 μg/mL, which were stored at 4° C. for further experiments.

(2) Preparation of Internal Standard Solution 0.0038 g of acetaminophen was accurately weighed, placed in a 25 mL volumetric flask, dissolved with methanol and diluted to the mark, shaken and formulated as a stock solution of acetaminophen at a concentration of 0.152 mg/mL. The stock solution of acetaminophen was diluted with methanol to a 15.2 ng/mL internal standard solution, which was stored at 4° C. for further experiments.

(3) Pretreatment of Carotid Sample

The animals were sacrificed before the administration and 2 h, 4 h, 8 h, 12 h, 24 h, 48 h, 72 h, and 168 h (seven days) after administration (one mouse at each time point). The carotid plaques were quickly removed and placed in normal saline, the surface water was absorbed by filter paper, 1 cm sample was cut from each plaque, the wet weight was weighed, 1 ml of normal saline was added and homogenized to prepare a homogenate.

1 ml of the homogenate was taken, 20 μL of methanol, 100 μL of the internal standard solution at a concentration of 15.2 ng/mL, 100 μL of 10% (v/v) formic acid aqueous solution, and 5 mL of ethyl acetate were added, mixed uniformly, and centrifuged at 14,000 rpm for 10 min. 4 ml of organic solution in the organic layer was taken and dried with nitrogen. Then, the same was dissolved in 200 μL of mobile phase (0.1% (v/v) formic acid aqueous solution and acetonitrile (40:60, v/v)), the solution was centrifuged at 14000 rpm for 10 min, and the supernatant was taken and transferred to a sample bottle for testing.

(4) Preparation of Samples for Standard Curve

10 μL of the serial concentrations of rosuvastatin solutions were taken and 500 μL of blank plasma was added, vortexed and mixed uniformly, and formulated as rosuvastatin simulated drug-containing plasma samples at concentrations of 200, 20, 10, 2.5, 1, 0.5, 0.2, 0.04, and 0.008 ng/mL, respectively. A standard curve was established following operations according to the plasma treatment (50 μL of the internal standard solution at a concentration of 15.2 ng/mL, 50 μL of 10% (v/v) formic acid aqueous solution, and 2.5 mL of ethyl acetate were added and mixed uniformly, the solution was centrifuged at 14,000 rpm for 10 min. 2 ml of organic solution in the organic layer was taken, the same was dried with nitrogen, then dissolved in 100 μL of mobile phase, and the same was centrifuged at 14,000 rpm for 10 min. The supernatant was taken and transferred to a sample bottle for testing). The linear regression was performed by weighted least squares method with the ratio of the rosuvastatin peak area to the internal standard peak area as the ordinate (y) and the blood concentration as the abscissa (x).

(5) Liquid Chromatography-Mass Spectrometry

The liquid phase separation was carried out using the Shimadzu modulaRLC system (Tokyo, Japan), and the system includes: 1 DGU-20A3R vacuum degasser, 2 LC-20ADXR solvent delivery modules, 1 SIL-20ACXR autosampler, 1 SPD-M20A PDA system and 1 CBM-20A controller. The liquid phase system was connected online with an ABSciex 5500 Qtrap mass spectrometer (FosteR-City, Calif., U.S.A.) equipped with an ESI interface. Analyst software (Version 1.6.2, ABSciex) was used for data acquisition and processing.

Chromatography was performed using Cortecs™ UPLC C18 column (150 mm×2.1 mm internal size (i.d.), 1.6 μm particle size) (Waters Corporation, U.S.A.), and the column temperature and sample chamber temperature were set to 40° C. and 4° C., respectively. The mobile phase was 0.1% (v/v) formic acid aqueous solution and acetonitrile (40:60, v/v) and the sample injection volume was 2 μl. The flow rate was 0.2 mL/min and the analysis time for a single sample was 4 min.

The mass spectrometry used the ESI source as the ion source, in the positive ion scan mode. The spray voltage was set to 4500 V and the source temperature was set to 500° C. Each compound was detected by multiple reaction monitoring (MRM). The ion channels of each component were: rosuvastatin calcium m/z 482.2-258.2, and acetaminophen m/z 152.2→110, respectively. The collision energy and cone voltage of each compound were optimized: rosuvastatin 43V and 100V, acetaminophen 23V and 100V. The retention time of rosuvastatin calcium and acetaminophen were 2.07 min and 1.49 min, respectively.

(6) Standard Curve

The linear range, correlation coefficient (r), linear equation and LLOQ of rosuvastatin are shown in Table 2. As shown in the table, the R value of rosuvastatin is greater than 0.999, which satisfies the requirements of quantitative analysis.

TABLE 2

Linear equation and LLOQ of rosuvastatin

| Compound | Linear range (ng/mL) | Correlation coefficient (r) | Regression equation | LLOQ (ng/mL) |
| --- | --- | --- | --- | --- |
| Rosuvastatin | 0.008-200 | 0.9999 | y = 129 x + 0.132 | 0.008 |

Percentage of drug exposure = weight of drug/weight of tissue.

Figure 8:
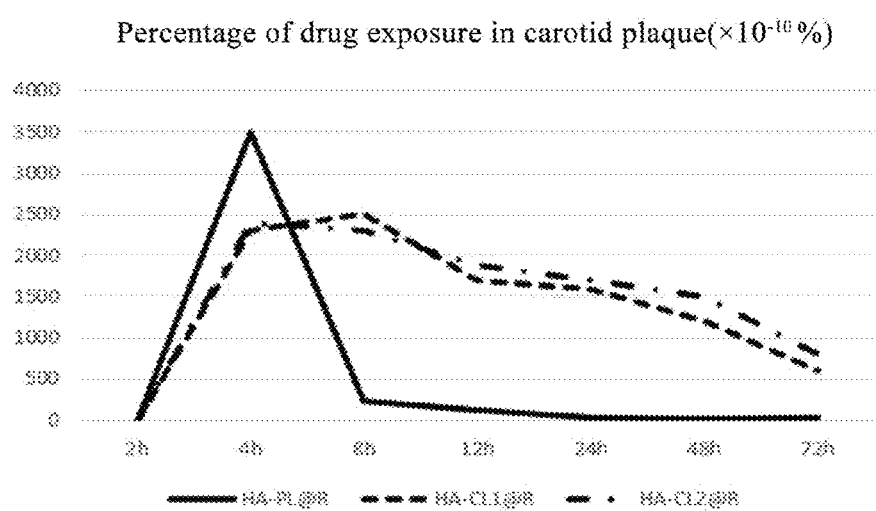
FIG. 8 is a graph showing the percentage of drug exposure in mice carotid plaque after administering the cerasome delivery system of the present disclosure and the liposome delivery system as a control.

Results are shown in FIG. 8. As shown in the figure, after injection of HA-PL@R, the concentration of rosuvastatin in the vulnerable plaque of the model mice rapidly decreases after reaching the peak in a short time, which indicates that liposome vesicles are unstable at vulnerable plaques, readily resulting in disintegration and rapid drug leakage. In contrast, after injection of HA-CL1@R and HA-CL2@R, the concentration of rosuvastatin in the vulnerable plaque of model mice reaches peaks at a relatively high speed and the concentration decreases gently over a relatively long period of time, which indicates that the cerasome delivery system of the present disclosure is able to remain stable in vulnerable plaques, thereby achieving the effect of sustained releasing the drug over a long period of time.

Example 5: Study on Targeting Mechanism

In this example, the density of CD44 on the surface of endothelial cells at vulnerable plaques and its affinity for HA are studied, thus providing an experimental basis for selecting CD44 within the vulnerable plaque as a target for the cerasome delivery system of the present disclosure for targeting the vulnerable plaque.
1) Comparison of CD44 Content on the Surface of Endothelial Cells at Arterial Vulnerable Plaques and on the Surface of Endothelial Cells of Normal Arterial Vessel Walls of Mice A mouse model of atherosclerotic vulnerable plaque was constructed according to the method described in Example 4 above. The endothelial cells of normal arterial vessels and endothelial cells at arterial vulnerable plaques of model mice are taken for CD44 content determination by immunohistochemical staining and image analysis, and the specific experimental method is as follow:

The mouse carotid atherosclerotic vulnerable plaque specimens were taken and fixed with 10 mL/L formaldehyde aqueous solution, embedded with paraffin, sectioned in 4 μm, dewaxed in a conventional manner, hydrated, and CD44 content was detected by streptavidin-biotin-peroxidase complex method (SABC). The specimen was immersed in 30 mL/L $H_2O_2$ aqueous solution to block the activity of endogenous peroxidase, and the specimen was placed in a citrate buffer for antigen microwave repair. Then 50 g/L bovine serum albumin (BSA) blocking solution was added dropwise and the sample was allowed to stand at room temperature for 20 min. Then, a murine anti-CD44 polyclonal antibody (1:100) was added dropwise, the sample was placed in a refrigerator at 4° C. overnight, and incubated at 37° C. for 1 h. The specimen was washed, then the biotinylated goat anti-mouse IgG was added dropwise and reacted at 37° C. for 30 min. Then, the same was washed with phosphate buffered saline (PBS), horseradish peroxidase-labeled SABC complex was added dropwise, and incubated at 37° C. for 20 min. Each step above was washed with PBS.

Finally, color development was performed with DAB (color developing is controlled under a microscope) and stained again with hematoxylin, the samples were then dehydrated and sealed. Sections were analyzed by immunohistochemical analysis system of BI-2000 image analysis system. Three sections were collected for endothelial cells of normal arterial vessels and endothelial cells at arterial vulnerable plaques, respectively, and five representative fields were randomly selected. The positive expression of CD44 is as follows: cell membrane and cytoplasm are yellow-brown/chocolate-brown and the background is clear, and the darker the color, the stronger the expression of CD44.

The negative expression of CD44 is as follows: no yellow-brown particles are found. The mean absorbance (A) values of positive cells in the endothelial cells of normal arterial vessels and endothelial cells at arterial vulnerable plaques were measured and compared. Results are shown in FIG. 9.

Figure 9:
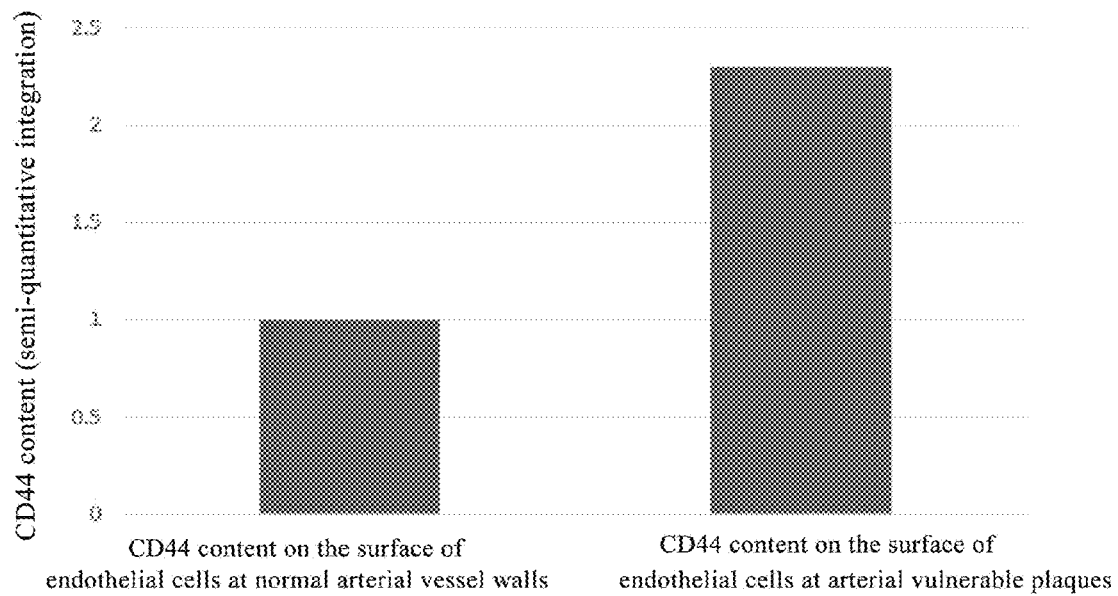
FIG. 9 is a graph showing the determination results (expressed as semi-quantitative integration) of CD44 content on the surface of endothelial cells of normal arterial vessel walls and on the surface of endothelial cells at arterial vulnerable plaques in mice model.

FIG. 9 shows the determination results of CD44 content (in semi-quantitative integration) on the surface of endothelial cells of normal arterial vessel walls and endothelial cells at arterial vulnerable plaques of model mice. As shown in the figure, the CD44 content on the surface of endothelial cells at arterial vulnerable plaques is approximately 2.3 times the CD44 content on the surface of endothelial cells of normal arterial vessels.
2a) Comparison of the Affinity of CD44 on the Surface of Endothelial Cells at Arterial Vulnerable Plaques and on the Surface of Endothelial Cells of Normal Arterial Vessel Walls of Mice for HA Endothelial cells at normal arterial vessel walls and endothelial cells at arterial vulnerable plaques of model mice were taken, and hyaluronic acid labeled with aminofluorescein at a concentration of 10 mg/ml (represented by "FL-HA") was added, and the sample was cultured in Dulberic modified Eagle's medium (DMEM) (containing calf serum with a volume fraction of 10%, 100 U/ml penicillin, 100 U/ml streptomycin) at 37° C., in 5% $CO_2$ incubator. After 30 minutes, the mean fluorescence intensity (MFI) was determined by flow cytometry (CytoFLEX, Beckman Coulter, U.S.A.), and the binding force integration of FL-HA on the surface of both cells was calculated (the binding force of endothelial cells of normal arterial vessel walls is set to 1). Results are shown in FIG. 10.

Figure 10:
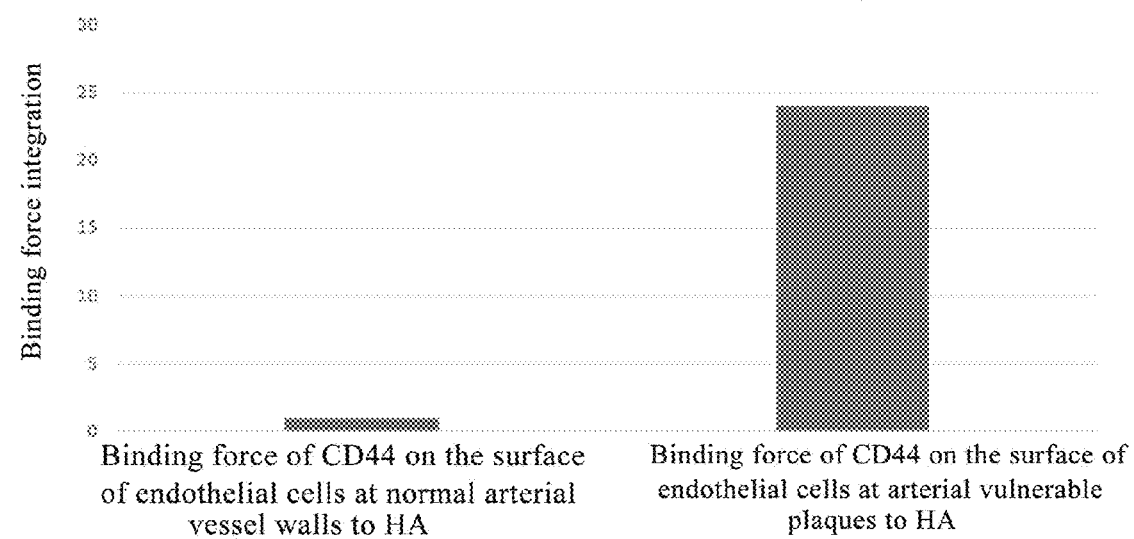
FIG. 10 is a graph showing the determination results (expressed as binding force integration) of the binding force of CD44 on the surface of endothelial cells of normal arterial vessel walls and on the surface of endothelial cells at arterial vulnerable plaques to HA in mice model.

As shown in FIG. 10, the binding force integration of FL-HA on the surface of endothelial cells at arterial vulnerable plaques is approximately 24 times that of endothelial cells of normal arterial vessel walls. This indicates that most of the CD44 on the surface of endothelial cells of normal arterial vessel walls are in a static state where it cannot bind to the ligand HA, while the CD44 on the surface of endothelial cells at arterial vulnerable plaques are activated by factors such as inflammatory factors in the internal environment, and the affinity for HA is significantly increased.
2b) Comparison of the Affinity of CD4 on the Surface of Endothelial Cells at Arterial Vulnerable Plaques and on the Surface of Endothelial Cells of Normal Arterial Vessel Walls of Mice for Ligand and Antibody Natural ligands for CD44 include: HA, GAG, collagen, laminin, fibronectin, selectin, osteopontin (OPN), and monoclonal antibodies HI44a, HI313, A3D8, H90, IM7, etc.

Endothelial cells at normal arterial vessel walls and endothelial cells at arterial vulnerable plaques of model mice were taken, and the ligand/antibody labeled with aminofluorescein at a concentration of 10 mg/ml was added, the sample was cultured in Dulberic modified Eagle's medium (DMEM) (containing calf serum with a volume fraction of 10%, 100 U/ml penicillin, 100 U/ml streptomycin) at 37° C., in 5% $CO_2$ incubator. After 30 minutes, the mean fluorescence intensity (MFI) was determined by flow cytometry (CytoFLEX, Beckman Coulter, U.S.A.), and the binding force integration of FL-ligand/antibody on the surface of both cells was calculated (the binding force of CD44 of endothelial cells of normal arterial vessel walls to ligand/antibody is set to 1). Results are shown in FIG. 11.

Figure 11:
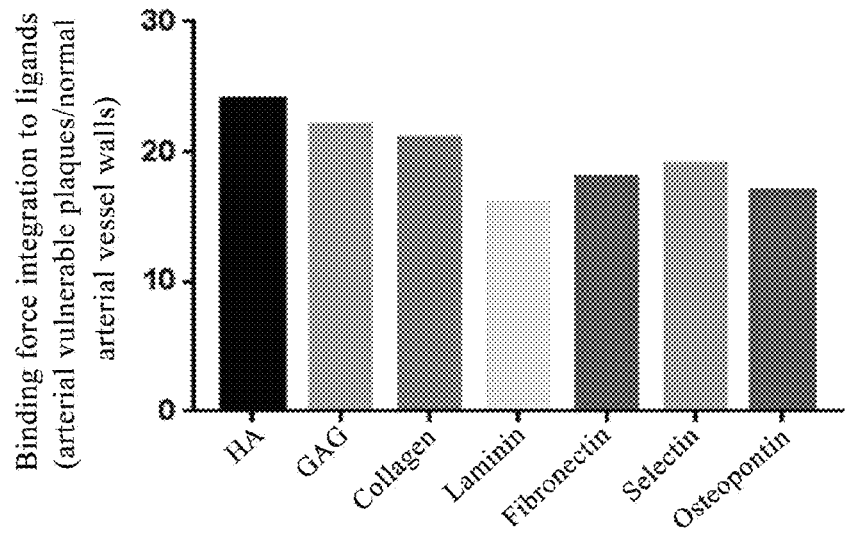
FIG. 11 is a graph showing the determination results (expressed as binding force integration) of the binding force of CD44 on the surface of endothelial cells of normal arterial vessel walls and on the surface of endothelial cells at arterial vulnerable plaques to various ligands/antibodies in mice model.
Figure 11:
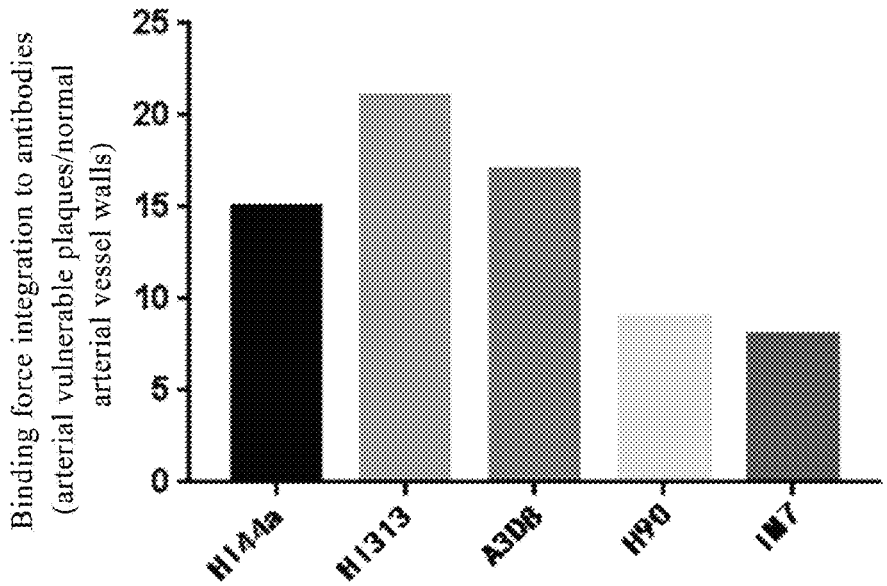

As shown in FIG. 11, the binding force integration of CD44 on the surface of endothelial cells at arterial vulnerable plaques to HA is approximately 24 times that of endothelial cells of normal arterial vessel walls. This indicates that most of the CD44 on the surface of endothelial cells of normal arterial vessel walls are in a static state where it cannot bind to the ligand HA, while the CD44 on the surface of endothelial cells at arterial vulnerable plaques are activated by factors such as inflammatory factors in the internal environment, and the affinity for HA is significantly increased.

Other ligands of CD44 have similar results to HA, and the binding force integration of CD44 on the surface of endothelial cells at vulnerable plaques to GAG is 22 times that of normal cells, and the binding force integration of CD44 on the surface of endothelial cells at vulnerable plaques to collagen is 21 times that of normal cells, the binding force integration of CD44 on the surface of endothelial cells at vulnerable plaques to laminin is 16 times that of normal cells, the binding force integration of CD44 on the surface of endothelial cells at vulnerable plaques to fibronectin is 18 times that of normal cells, the binding force integration of CD44 on the surface of endothelial cells at vulnerable plaques to selectin is 19 times that of normal cells, and the binding force integration of CD44 on the surface of endothelial cells at vulnerable plaques to osteopontin is 17 times that of normal cells.

Similar results were observed for monoclonal antibodies of CD44: the binding force integration of CD44 on the surface of endothelial cells at vulnerable plaques to HI44a is 15 times that of normal cells, the binding force integration of CD44 on the surface of endothelial cells at vulnerable plaques to HI313 is 21 times that of normal cells, the binding force integration of CD44 on the surface of endothelial cells at vulnerable plaques to A3D8 is 17 times that of normal cells, the binding force integration of CD44 on the surface of endothelial cells at vulnerable plaques to H90 is 9 times that of normal cells, and the binding force integration of CD44 on the surface of endothelial cells at vulnerable plaques to IM7 is 8 times that of normal cells.

3a) Comparison of the Affinity of CD44 on the Surface of Macrophages Outside the Plaque and that of Macrophages Inside Arterial Vulnerable Plaques for HA Intraperitoneal macrophages and macrophages inside arterial vulnerable plaques of model mice were taken, and hyaluronic acid labeled with aminofluorescein at a concentration of 10 mg/ml (represented by "FL-HA") was added, the sample was cultured in DMEM (containing calf serum with a volume fraction of 10%, 100 U/ml penicillin, 100 U/ml streptomycin) at 37° C., in 5% $CO_2$ incubator. After 30 minutes, the mean fluorescence intensity (MFI) was determined by flow cytometry (CytoFLEX, Beckman Coulter, U.S.A.), and the binding force integration of FL-HA on the surface of both cells was calculated (the affinity of CD44 on the surface of macrophages outside the plaque for HA is set to 1). Results are shown in FIG. 12.

Figure 12:
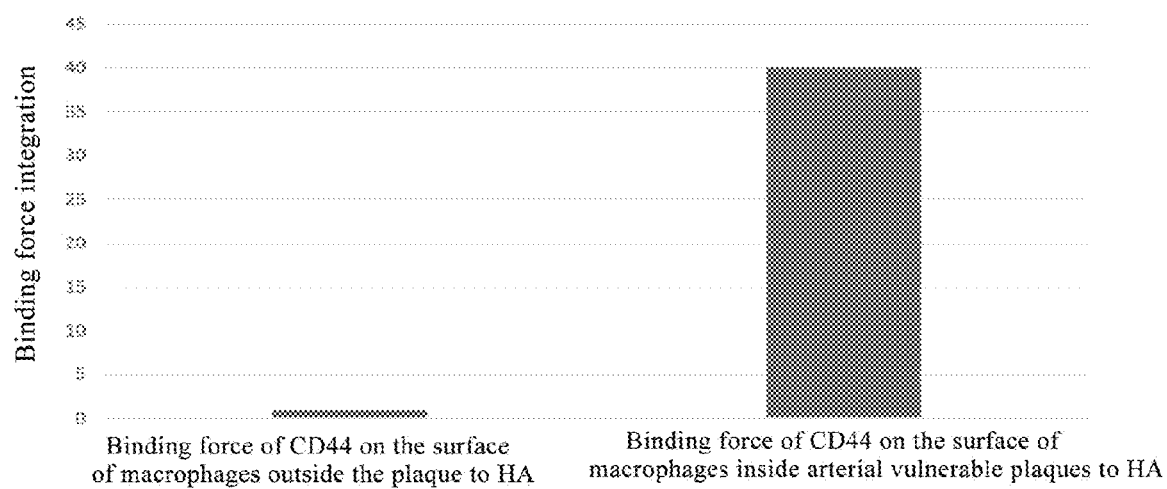
FIG. 12 is a graph showing the determination results (expressed as binding force integration) of the binding force of CD44 on the surface of macrophages outside and inside arterial vulnerable plaques to HA in mice model.

As shown in FIG. 12, the binding force of FL-HA on the surface of macrophages inside arterial vulnerable plaques is approximately 40 times that of macrophages outside the plaque. This indicates that the CD44 on the surface of macrophages inside arterial vulnerable plaques are also activated by factors such as inflammatory factors in the internal environment, and the affinity for HA is significantly increased.

Based on the results of the above experiments, the following conclusions can be drawn: compared with normal cells (such as endothelial cells of normal arterial vessel walls, macrophages outside the plaque), the density of CD44 on the surface of cells in vulnerable plaques (including endothelial cells, macrophages, etc., which are important for the development of arterial vulnerable plaques) is significantly increased, and its affinity for HA is significantly enhanced, thus the specific affinity of CD44 inside arterial vulnerable plaques for HA ligands is much higher than that of normal cells, making it very advantageous as an excellent target for the cerasome delivery system of the present disclosure for targeting vulnerable plaques.

3b) Comparison of the Affinity of CD44 on the Surface of Macrophages Outside the Plaque and that of Macrophages Inside Arterial Vulnerable Plaques for a Ligand/an Antibody Intraperitoneal macrophages and macrophages inside arterial vulnerable plaques of model mice were taken, and the ligand/antibody labeled with aminofluorescein at a concentration of 10 mg/ml was added, the sample was cultured in DMEM (containing calf serum with a volume fraction of 10%, 100 U/ml penicillin, 100 U/ml streptomycin) at 37° C., in 5% $CO_2$ incubator. After 30 minutes, the mean fluorescence intensity (MFI) was determined by flow cytometry (CytoFLEX, Beckman Coulter, U.S.A.), and the binding force integration of FL-HA on the surface of both cells was calculated (the affinity of CD44 on the surface of macrophages outside the plaque for a ligand/an antibody is set to 1). Results are shown in FIG. 13.

Figure 13:
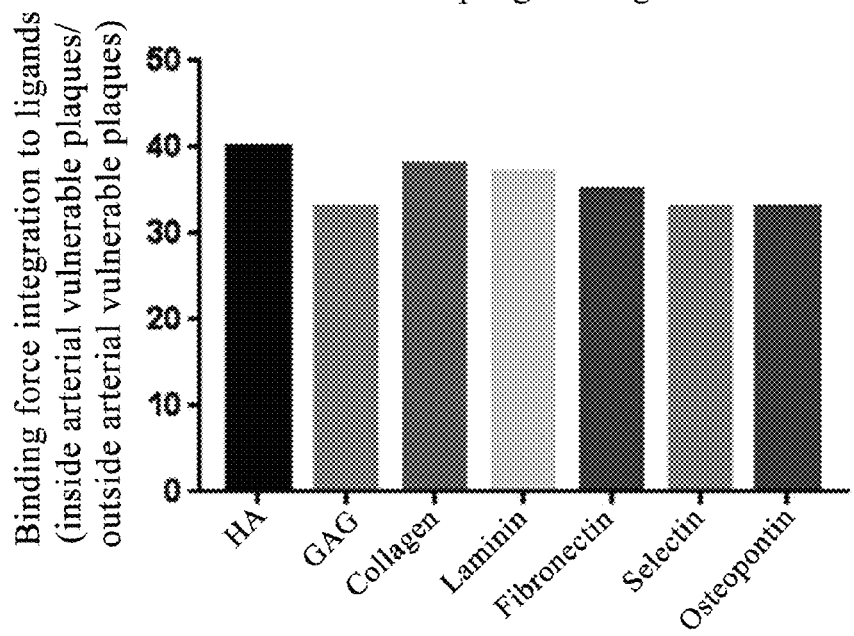
FIG. 13 is a graph showing the determination results (expressed as binding force integration) of the binding force of CD44 on the surface of macrophages outside and inside arterial vulnerable plaques to various ligands/antibodies in mice model.
Figure 13:
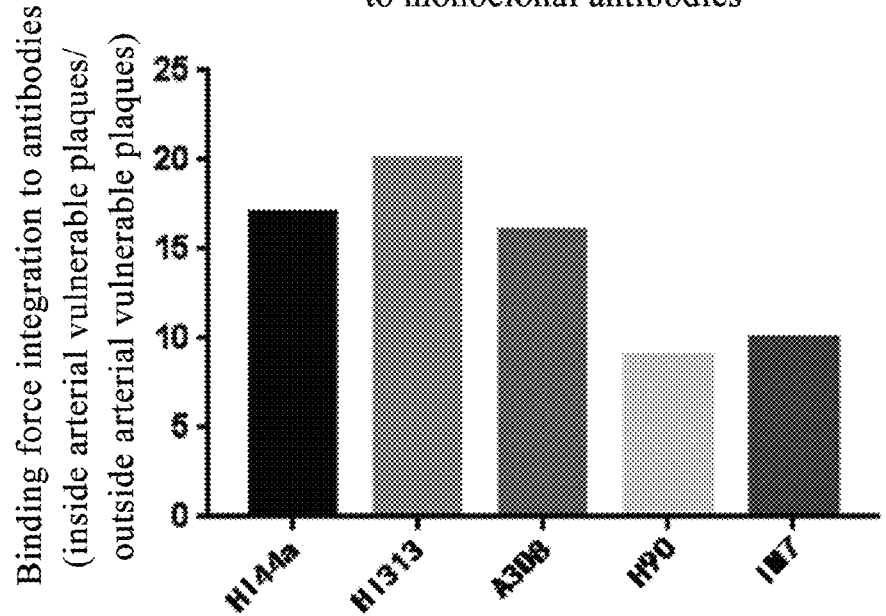

As shown in FIG. 13, the binding force of CD44-HA on the surface of macrophages inside arterial vulnerable plaques is approximately 40 times the binding force of CD44-HA on the surface of macrophages outside the plaques. This indicates that the CD44 on the surface of macrophages inside arterial vulnerable plaques are also activated by factors such as inflammatory factors in the internal environment, and the affinity for HA is significantly increased.

Other ligands of CD44 have similar results to HA, and the binding force integration of CD44 on the surface of macrophages at vulnerable plaques to GAG is 33 times that of normal cells, and the binding force integration of CD44 on the surface of macrophages at vulnerable plaques to collagen is 38 times that of normal cells, the binding force integration of CD44 on the surface of macrophages at vulnerable plaques to laminin is 37 times that of normal cells, the binding force integration of CD44 on the surface of macrophages at vulnerable plaques to fibronectin is 35 times that of normal cells, the binding force integration of CD44 on the surface of macrophages at vulnerable plaques to selectin is 33 times that of normal cells, and the binding force integration of CD44 on the surface of macrophages at vulnerable plaques to osteopontin is 33 times that of normal cells.

Similar results were observed for monoclonal antibodies of CD44: the binding force integration of CD44 on the surface of macrophages at vulnerable plaques to HI44a is 17 times that of normal cells, the binding force integration of CD44 on the surface of macrophages at vulnerable plaques to HI313 is 20 times that of normal cells, the binding force integration of CD44 on the surface of macrophages at vulnerable plaques to A3D8 is 16 times that of normal cells, the binding force integration of CD44 on the surface of macrophages at vulnerable plaques to H90 is 9 times that of normal cells, and the binding force integration of CD44 on the surface of macrophages at vulnerable plaques to IM7 is 10 times that of normal cells.

Based on the results of the above experiments, the following conclusions can be drawn: compared with normal cells (such as endothelial cells of normal arterial vessel walls, macrophages outside the plaque), the density of CD44 on the surface of cells in vulnerable plaques (including endothelial cells, macrophages, etc., which are important for the development of arterial vulnerable plaques) is significantly increased, and its affinity for a ligand is significantly enhanced, thus the specific affinity of CD44 inside arterial vulnerable plaques for a ligand is much higher than that of normal cells, making it very advantageous as an excellent target for the cerasome delivery system of the present disclosure for targeting vulnerable plaques.

Example 6: In Vivo Experiment about the Effect of the Cerasome Delivery System of the Present Disclosure on Arterial Vulnerable Plaques The purpose of this example is to verify the in vivo therapeutic effect of the cerasome delivery system of the present disclosure that is loaded with a therapeutic agent on arterial vulnerable plaques.

Experimental Method:

(1) A normal saline solution of free rosuvastatin was prepared, and the cerasome delivery system HA-CL1@R loaded with a therapeutic agent, the cerasome delivery system HA-CL1@R+LMHA loaded with a therapeutic agent and a small-molecular hyaluronic acid, the cerasome delivery system HA-CL1@R+S loaded with a therapeutic agent and a CD44 activator, the liposome delivery system HA-PL@R loaded with a therapeutic agent and hyaluronic acid nanomicelle system PDLLA/Chol-HA@R (as a comparative example) were prepared by the method described in the above Example 2.

Preparation of hyaluronic acid nanomicelle system (PDLLA/Chol-HA@R): 1 g of cholesterol was dissolved in 30 mL of acetone, and 1 g of succinic anhydride was added. The reaction solution was stirred at 70° C. for 3 h. The solvent was removed by reduced pressure distillation, and the crude product was dissolved and recrystallized from water/anhydrous ethanol (1:10) to give the cholesterol succinate. 500 mg of cholesterol succinate was weighed and dissolved in 20 mL of anhydrous chloroform, and 6 mL of chloroform containing 1 mL of thionyl chloride was added dropwise. After completion of the dropwise addition, the temperature of the system was raised to 60° C., and the reaction was lasted for 5 hours. The unreacted thionyl chloride and trichloromethane were removed by reduced pressure distillation to give a pale green oil. 500 mg of hyaluronic acid (10 kD) was weighed and dissolved in 60 mL of dimethyl sulfoxide, and 1 mL of triethylamine was added, 5 mL of cholesterol succinate acyl chloride in dimethyl sulfoxide solution was measured, which was slowly added under protection of nitrogen to the mixture. The system was reacted at a constant temperature of 80° C. for 7 h. After the reaction was completed, the heating was stopped. The reaction product was dialyzed against water for 72 h before being freeze-dried to obtain cholesterol-modified hyaluronic acid (Chol-HA).

50 mg of Chol-HA and 50 mg of polylactic acid (PDLLA) were weighed and dissolved together in 10 mL of DMF, the reaction solution was stirred on a magnetic stirrer for 24 h until completely mixed, the obtained polymer solution was poured into a dialysis bag with a cut-off molecular weight of 3000 and dialyzed against 500 mL of deionized water for 4 hours, the aqueous phase was then replaced with a 2 wt % rosuvastatin solution and dialysis was continued for 48 h. The dialysis bag was then immediately placed in 20 mL of rosuvastatin solution (1 mg mL$^{-1}$) and incubated for 24 h, and then dialyzed against 1 L of deionized water for 4 h, during which the deionized water was changed once every hour to remove the unencapsulated drug. The obtained nanovesicle solution was removed from the dialysis bag and lyophilized to obtain a nanocarrier PDLLA/Chol-HA@R loaded with rosuvastatin.

(2) Establishment of ApoE−/− Mouse Model of Arterial Vulnerable Plaque:

SPF-grade ApoE−/− mice (30 mice, 5-6 weeks old, weight 20 f 1 g) were taken as experimental animals. The mice were fed with an adaptive high-fat diet (fat 10% (w/w), cholesterol 2% (w/w), sodium cholate 0.5% (w/w), and the rest being normal feed for mice) for 4 weeks, and then anaesthetized via intraperitoneal injection of 1% sodium pentobarbital (prepared by adding 1 mg of sodium pentobarbital to 100 ml of normal saline) at a dose of 40 mg/kg. Then, the mice were fixed on the surgical plate in the supine position, disinfected around the neck with 75% (v/v) alcohol, the neck skin was cut longitudinally, and the anterior cervical gland was bluntly separated, and the beating left common carotid artery can be observed on the left side of the trachea. The common carotid artery was carefully separated to the bifurcation. A silicone cannula with a length of 2.5 mm and an inner size of 0.3 mm was placed on the outer periphery of the left common carotid artery. The proximal and distal segments of the cannula were narrowed and fixed by filaments. Local tightening causes rapid blood flow in the proximal end with increased shear force, and thus damage to the intima of the blood vessel. The carotid artery was repositioned and the neck skin was intermittently sutured. All operations were performed under a 10×stereomicroscope. After awakened from the surgery, the mice were returned to the cage, where the ambient temperature was maintained at 20-25° C., and the light was kept under a 12 h/12 h light/dark cycle. At the 4th week after the surgery, lipopolysaccharide (LPS) (1 mg/kg in 0.2 ml phosphate buffered saline, Sigma, U.S.A.) was injected intraperitoneally twice a week for 10 weeks to induce chronic inflammation. At the 8th week after the surgery, mice were placed in a 50 ml syringe (sufficient vents reserved) to trigger restrictive mental stress, 6 hours/day, 5 days per week for a total of 6 weeks. The mouse model of atherosclerotic vulnerable plaque was completed at the 14th week after the surgery.

(3) Grouping and Treatment of Experimental Animals:

The experimental animals were randomly divided into the following groups, 6 mice in each group:

control group of vulnerable plaque model: this group of animals do not undergo any therapeutic treatment;

group intragastrically administered with rosuvastatin: treatment by intragastric administration at a dose of 5 mg rosuvastatin per kg body weight;

group intravenously administered with rosuvastatin: treatment by intravenous administration at a dose of 5 mg rosuvastatin per kg body weight;

HA-PL@R group: treatment by intravenous administration at a dose of 5 mg rosuvastatin per kg body weight;

PDLLA/Chol-HA@R group: treatment by intravenous administration at a dose of 5 mg rosuvastatin per kg body weight;

HA-CL1@R group: treatment by intravenous administration at a dose of 5 mg rosuvastatin per kg body weight;

HA-CL1@R+LMHA group: treatment by intravenous administration of 5 mg rosuvastatin and 1.25 mg small-molecular hyaluronic acid having a molecular weight of 3411 Da per kg body weight;

HA-CL1@R+S group: treatment by intravenous administration at a dose of 5 mg rosuvastatin and 1.75 mg CD44 antibody mAb per kg body weight.

Except for the control group of vulnerable plaque model, the treatment group was treated once every other day for a total of 5 treatments. For animals in each group, carotid MRI scans were performed before and after treatment to detect plaque and lumen area, and the percentage of plaque progression was calculated.

Percentage of plaque progression=(plaque area after treatment−plaque area before treatment)/lumen area.

Figure 14:
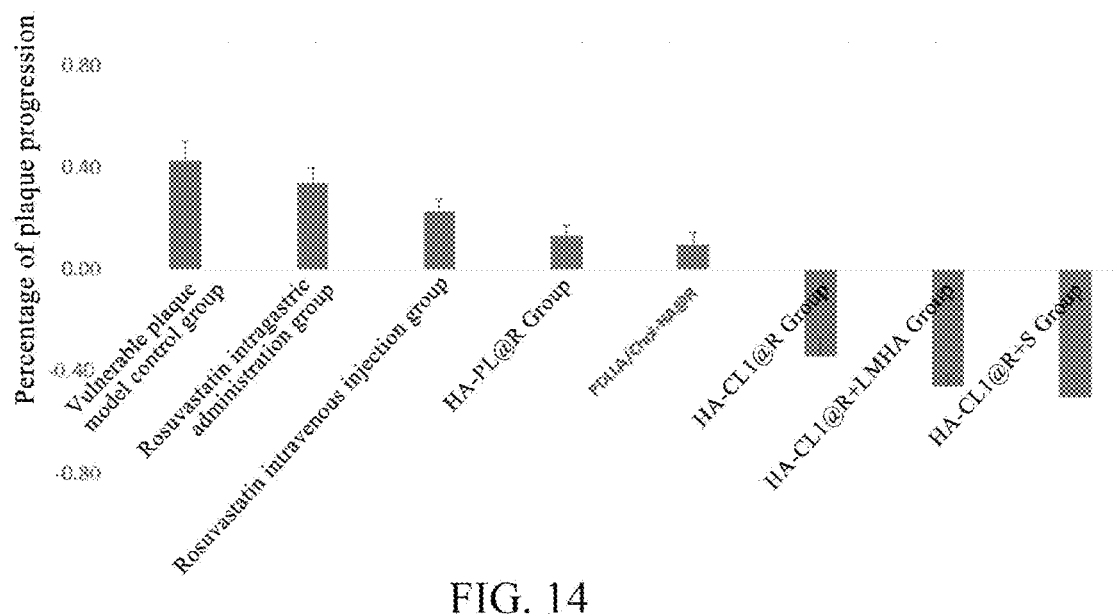
FIG. 14 is a graph showing the in vivo therapeutic effect (expressed as percentage of plaque progression) of the cerasome delivery system of the present disclosure on carotid vulnerable plaques in mice model.

Experimental Results:

FIG. 14 displays the in vivo therapeutic effect of the cerasome delivery system of the present disclosure loaded with a therapeutic agent on arterial vulnerable plaques. As shown in the figure, for arterial vulnerable plaques in mice, whether administered by intragastric administration or intravenous administration, free rosuvastatin shows a certain therapeutic effect, but it could not prevent the continued growth of vulnerable plaques. Compared with free rosuvastatin, when administered in a liposome delivery system or a hyaluronic acid nanomicelle delivery system, the therapeutic effect of rosuvastatin on vulnerable plaques has been improved to some extent, but it still cannot prevent the continued growth of the vulnerable plaques. However, when formulated in the cerasome delivery system of the present disclosure, the therapeutic effect of rosuvastatin on vulnerable plaques has been significantly improved and has been shown the therapeutic effect of reversing the plaque growth (i.e., reducing the plaque). In particular, the present inventors have unexpectedly discovered that when rosuvastatin is formulated in combination with the small-molecular hyaluronic acid or CD44 activator-CD44 antibody mAb in the cerasome delivery system for combination administration, the therapeutic effect of rosuvastatin on arterial vulnerable plaques in mice is very significant. In summary, administration of a therapeutic agent using the cerasome delivery system of the present disclosure significantly reverses the growth of arterial vulnerable plaques as compared to administration of a free drug and using liposome delivery systems, with a better therapeutic effect.

In addition, similar studies have found that the therapeutic effect of the cerasome delivery systems of the present disclosure HA-CL1@R, HA-CL2@R and HA-CL3@R on arterial vulnerable plaques are similar, which further indicates that the three cerasome delivery systems of the present disclosure HA-CL1@R, HA-CL2@R and HA-CL3@R have similar drug release mechanisms and properties.

Example 7: In Vivo Tracing Experiment of the Cerasome Delivery System of the Present Disclosure on Arterial Vulnerable Plaques The purpose of this example is to verify the in vivo tracing effect of the cerasome delivery system of the present disclosure loaded with a tracer on arterial vulnerable plaques.

Experimental Method:

(1) A commercially available nanogold solution was used, and the cerasome delivery system HA-CL1@AuNPs loaded with a CT tracer nanogold, the cerasome delivery system HA-CL1@AuNPs+S loaded with a tracer and a CD44 activator, and the non-targeting cerasome delivery system CL1@AuNPs loaded with a tracer (as a comparative example) were prepared by the method described in the above Example 2.

(2) A mouse model of atherosclerotic vulnerable plaque was constructed according to the method described in Example 4 above.

(3) The model mice were fed with a high-fat diet (same as in Example 4) for 16 weeks. 24 model mice were randomly divided into the free nanogold particle group (6 mice, given the commercially available nanogold solution, the dosage of nanogold was 0.1 mg/kg body weight), the CL1@AuNPs group (6 mice, given CL1@AuNPs, the dosage of nanogold was 0.1 mg/kg body weight), the HA-CL1@AuNPs group (6 mice, given HA-CL1@AuNPs, the dosage of nanogold was 0.1 mg/kg body weight) and HA-CL1@AuNPs+S group (6 mice, given HA-CL1@AuNPs+S, the dosage of nanogold was 0.1 mg/kg body weight, and the dosage of CD44 activator-CD44 antibody mAb was about 0.07 mg/kg body weight). Animals in each experimental group were injected with the corresponding tracer through the tail vein, and CT imaging was performed before administration and 4 hours after administration to observe the identification of atherosclerotic vulnerable plaque in each group.

Figure 15:
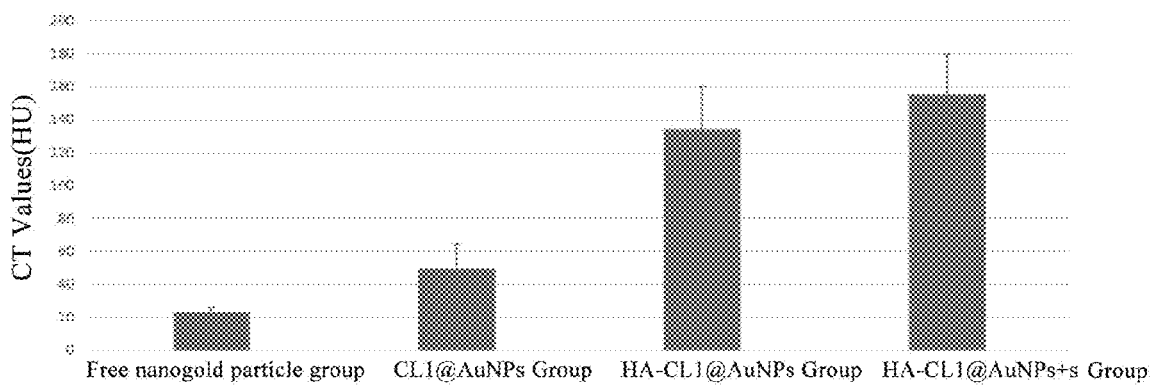
FIG. 15 is a graph showing the in vivo tracing effect (expressed as CT values) of the cerasome delivery system of the present disclosure on carotid vulnerable plaques in mice model.

Experimental Results:

FIG. 15 displays the in vivo tracing effect of the cerasome delivery system of the present disclosure loaded with a tracer on arterial vulnerable plaques.

As shown in the figure, the free nanogold particles show a certain tracing effect on arterial vulnerable plaques in mice. Compared with the free nanogold particles, when the nanogold is formulated in a non-targeting cerasome delivery system, the tracing effect of the nanogold on vulnerable plaques has been improved to some extent. When the nanogold is formulated in the cerasome delivery system of the present disclosure whose surface is modified with a targeting ligand hyaluronic acid, the tracing effect of the nanogold on vulnerable plaques has been significantly improved. In particular, the present inventors have unexpectedly discovered that when the nanogold is formulated in combination with a CD44 activator-CD44 antibody mAb in a cerasome delivery system for combination administration, the tracing effect of the nanogold on arterial vulnerable plaques in mice is very significant. In summary, administration in the cerasome delivery system of the present disclosure whose surface is modified with a targeting ligand hyaluronic acid can significantly improve the recognition effect of the nanogold on vulnerable plaques compared to the administration of the free nanogold particles and in non-targeting cerasome delivery systems, resulting in better tracing effect.

In addition, similar studies have found that the tracing effect of the cerasome delivery systems of the present disclosure, HA-CL1@AuNPs, HA-CL2@AuNPs and HA-CL3@AuNPs which are loaded with a tracer, on arterial vulnerable plaques are similar, which further indicates that the three cerasome delivery systems of the present disclosure HA-CL1@AuNPs, HA-CL2@AuNPs and HACL3@AuNPs have similar drug release mechanisms and properties.

Example 8: In Vivo Tracing (CT Tracing) Experiment of the Cerasome-HA-Iodixanol Delivery System of the Present Disclosure on Arterial Vulnerable Plaques The purpose of this example is to verify the in vivo tracing effect of the cerasome delivery system of the present disclosure loaded with a CT tracer on arterial vulnerable plaques.

Experimental Method:

(1) A commercially available iodixanol bulk drug was used, and the cerasome delivery system HA-CL1@I loaded with a CT tracer, the cerasome delivery system HA-CL1@I+S loaded with a tracer and a CD44 activator, and the non-targeting cerasome delivery system CL1@I loaded with a tracer (as a comparative example) were prepared by the method described in the above Example 2.

(2) A mouse model of atherosclerotic vulnerable plaque was constructed according to the method described in Example 6 above.

Figure 16:
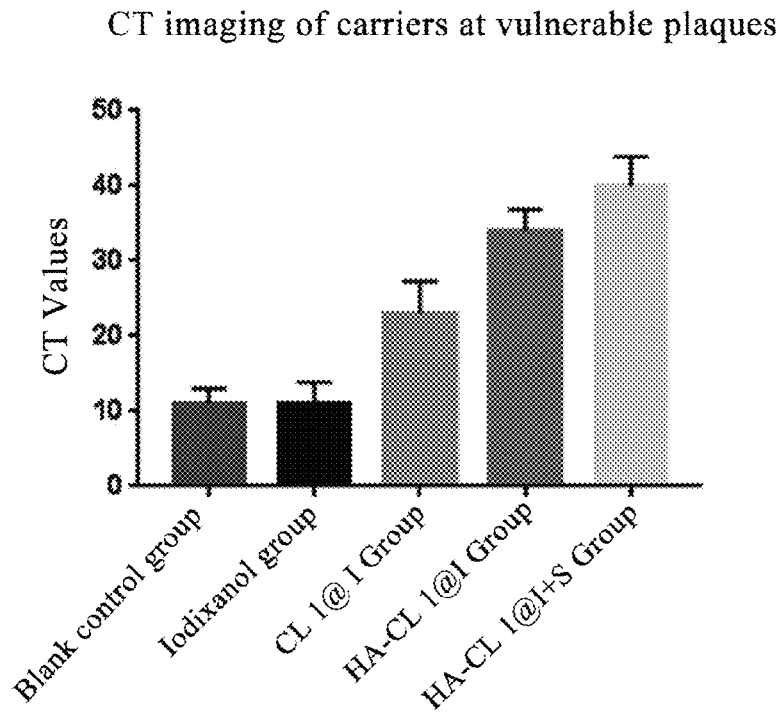
FIG. 16 shows the in vivo CT tracing of the cerasome-HA-iodixanol delivery system for arterial vulnerable plaques.

(3) The model mice were fed with a high-fat diet (same as in Example 6) for 16 weeks. 30 model mice were randomly divided into the blank group (6 mice), the iodixanol group (6 mice, given the commercially available iodixanol bulk drug, and the dosage of iodixanol was 0.66 mg/kg body weight), the CL1@I group (6 mice, given CL1@I, and the dosage of iodixanol was 0.66 mg/kg body weight), the HA-CL1@I group (6 mice, given HA-CL1@I, and the dosage of iodixanol was 0.66 mg/kg body weight), and HA-CL1@I+S group (6 mice, given HA-CL1@I+S, the dosage of iodixanol was 0.66 mg/kg body weight, and the dosage of CD44 activator-LPS was about 0.023 mg/kg body weight). Animals in each experimental group were injected with the corresponding tracer through the tail vein, and CT imaging was performed before administration and 72 hours after administration to observe the identification of atherosclerotic vulnerable plaque in each group.
Experimental Results:

FIG. 16 displays the in vivo tracing effect of the cerasome delivery system of the present disclosure loaded with a tracer on arterial vulnerable plaques. As shown in the figure, intravenous administration of iodixanol does not show any tracing effect on arterial vulnerable plaques in mice. Compared with intravenous administration of iodixanol, when it is loaded in a non-targeting cerasome delivery system, the tracing effect of iodixanol on vulnerable plaques has been improved to some extent. When iodixanol is formulated in the cerasome delivery system of the present disclosure whose surface is modified with a targeting ligand hyaluronic acid, the tracing effect of iodixanol on vulnerable plaques has been significantly improved. In particular, the present inventors have unexpectedly discovered that when iodixanol is formulated in combination with a CD44 activator-LPS in a cerasome delivery system for combination administration, the tracing effect of iodixanol on arterial vulnerable plaques in mice is very significant. In summary, administration in the cerasome delivery system of the present disclosure whose surface is modified with a targeting ligand hyaluronic acid can significantly improve the recognition effect of iodixanol on vulnerable plaques compared to the free iodixanol and in non-targeting cerasome delivery systems, resulting in better tracing effect.

Example 9: In Vivo Tracing (MRI Tracing) Experiment of the Cerasome-HA-Gadoterate Meglumine Delivery System of the Present Disclosure on Arterial Vulnerable Plaques The purpose of this example is to verify the in vivo tracing effect of the cerasome delivery system of the present disclosure loaded with an MRI tracer on arterial vulnerable plaques.
Experimental Method:

(1) A commercially available bulk drug gadoterate meglumine was used, and the cerasome delivery system loaded with an MRI tracer and a blank cerasome delivery system (as a comparative example) were prepared by the method described in the above Example 2.

(2) A mouse model of atherosclerotic vulnerable plaque was constructed according to the method described in Example 6 above.

Figure 17:
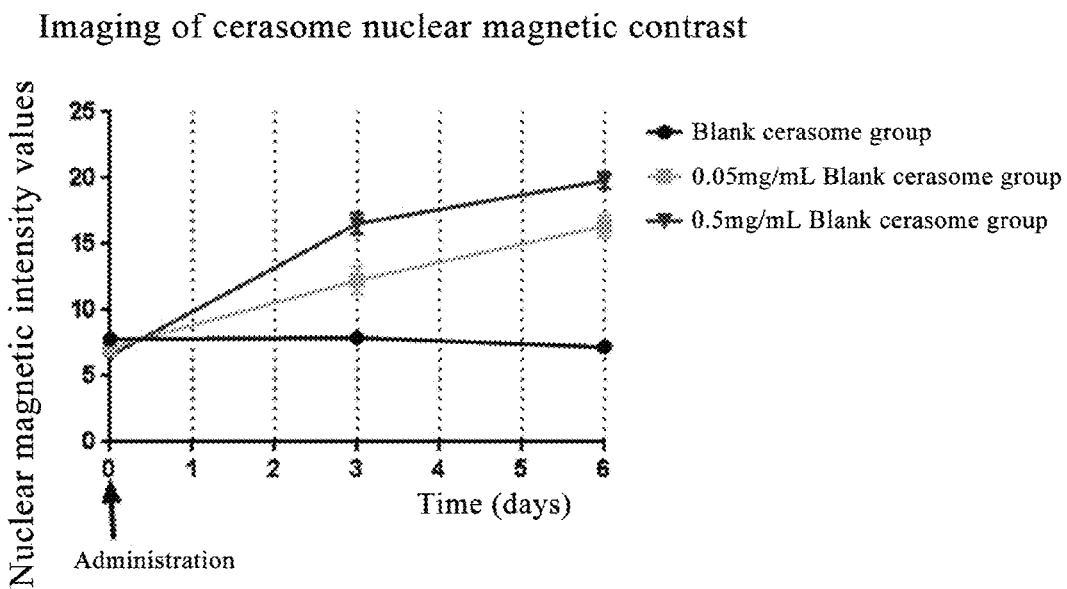
FIG. 17 shows the in vivo MRI tracing of the cerasome-HA-gadoterate meglumine delivery system for arterial vulnerable plaques.

(3) The model mice were fed with a high-fat diet (same as in Example 6) for 16 weeks. 18 model mice were randomly divided into the blank cerasome group (6 mice), the cerasome group with a low concentration of gadoterate meglumine (6 mice, given a commercially available gadoterate meglumine bulk drug, the concentration of gadoterate meglumine was 0.05 mg/ml, and the dosage is 10 ml/kg), and the cerasome group with a high concentration of gadoterate meglumine (6 mice, given a commercially available gadoterate meglumine bulk drug, the concentration of gadoterate meglumine was 0.5 mg/ml, and the dosage is 10 ml/kg). Animals in each experimental group were injected with the corresponding tracer through the tail vein, and MRI imaging was performed before administration and at multiple time points after administration to observe the identification of atherosclerotic vulnerable plaque in each group.
Experimental Results:

FIG. 17 displays the in vivo tracing effect of the cerasome delivery system of the present disclosure loaded with a tracer on arterial vulnerable plaques. As shown in the figure, the blank cerasome does not show any tracing effect on arterial vulnerable plaques in mice. Compared with the blank cerasome group, when gadoterate meglumine is loaded in a targeting cerasome delivery system, the tracing effect of gadoterate meglumine on vulnerable plaques has been significantly improved, and in a dosage-dependent manner. In summary, compared with the blank cerasome delivery system, administration in the cerasome-HA-gadoterate meglumine delivery system of the present disclosure may show recognition effect on arterial vulnerable plaques, resulting in a better MRI tracing effect.

Example 10: In Vivo Tracing (MRI Tracing) Experiment of the Multiple CD44 Monoclonal Antibodies-Cerasome-Gadoterate Meglumine Delivery System of the Present Disclosure on Arterial Vulnerable Plaques The purpose of this example is to verify the in vivo tracing effect of the nano delivery system of the present disclosure, which is loaded with an MRI tracer and assembled with a variety of different CD44 monoclonal antibodies on the surface, on arterial vulnerable plaques.
Experimental Method:

(1) A commercially available bulk drug gadoterate meglumine was used, and the cerasome nano delivery systems loaded with an MRI tracer and modified with different CD44 monoclonal antibodies as targeting probes were prepared by the method described in the above Example 2.

(2) A mouse model of atherosclerotic vulnerable plaque was constructed according to the method described in Example 6 above.

(3) The model mice were fed with a high-fat diet (same as in Example 6) for 16 weeks. 24 model mice were randomly divided into the blank group (6 mice), the gadoterate meglumine-cerasome-HI44a group (6 mice, given a commercially available gadoterate meglumine bulk drug, the concentration of gadoterate meglumine was 0.5 mg/ml, and the dosage was 10 ml/kg), the gadoterate meglumine-cerasome-A3D8 group (6 mice, given a commercially available gadoterate meglumine bulk drug, the concentration of gadoterate meglumine was 0.5 mg/ml, and the dosage was 10 ml/kg), and the gadoterate meglumine-cerasome-H90 group (6 mice, given a commercially available gadoterate meglumine bulk drug, the concentration of gadoterate meglumine is 0.5 mg/ml, and the dosage was 10 ml/kg). Animals in each experimental group were injected with the corresponding tracer through the tail vein, and MRI imaging was performed before administration and at multiple time points after administration to observe the recognition of atherosclerotic vulnerable plaque in each group.

Figure 18:
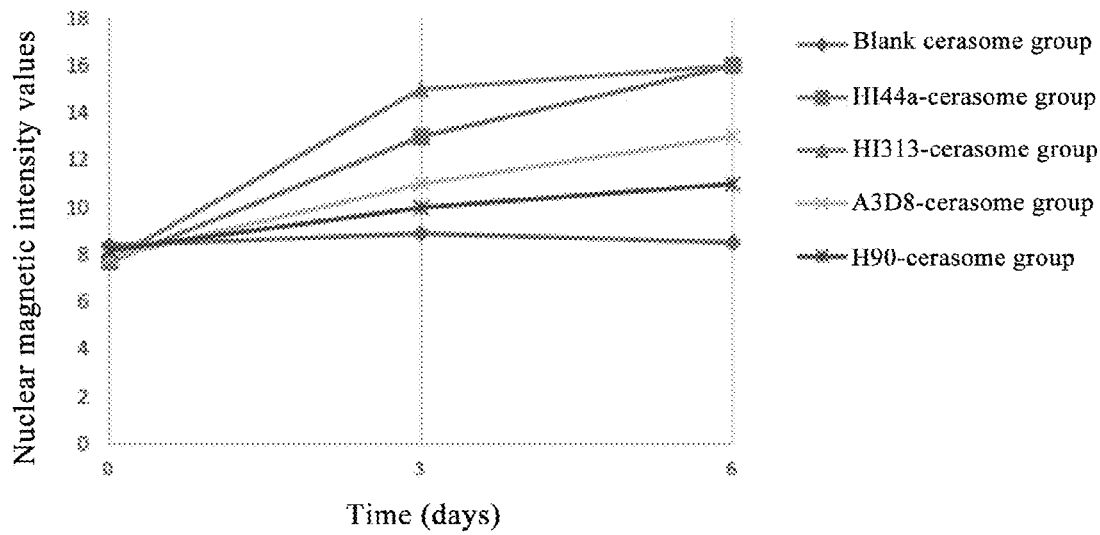
FIG. 18 shows the in vivo MRI tracing of various CD44 monoclonal antibodies-cerasome-gadoterate meglumine delivery system for arterial vulnerable plaques.

Experimental Results:

FIG. 18 displays the in vivo tracing effect of the cerasome delivery system of the present disclosure with multiple CD44 monoclonal antibodies as probes on arterial vulnerable plaques. In summary, compared with the blank cerasome delivery system, administration with the cerasome nano system of the present disclosure with multiple CD44 monoclonal antibodies as targeting probes (including gadoterate meglumine-cerasome-HI44a nano system, gadoterate meglumine-cerasome-A3D8 nano system, gadoterate meglumine-cerasome-H90 nano system) may show recognition effect on arterial vulnerable plaques, resulting in a better MRI tracing effect.

Example 11: In Vivo Tracing (MRI Tracing) Experiment of the Various CD44 Ligands-Cerasome-Gadodiamide Delivery System of the Present Disclosure on Arterial Vulnerable Plaques The purpose of this example is to verify the in vivo tracing effect of the nano delivery system of the present disclosure, which is loaded with an MRI tracer and assembled with a variety of different CD44 ligands on the surface, on arterial vulnerable plaques.

Experimental Method:

(1) A commercially available bulk drug gadodiamide was used, and cerasome nano delivery systems loaded with an MRI tracer and different CD44 ligands as targeting probes were prepared by the method described in the above Example 2.

(2) A mouse model of atherosclerotic vulnerable plaque was constructed according to the method described in Example 6 above.

(3) The model mice were fed with a high-fat diet (same as in Example 6) for 16 weeks. 42 model mice were randomly divided into the blank cerasome group (6 mice), the HA-cerasome group (6 mice), the collagen-gadodiamide-cerasome group (6 mice, given a commercially available gadodiamide bulk drug, the concentration of gadodiamide was 0.5 mg/ml, and the dosage was 10 ml/kg), the laminin-gadodiamide-cerasome group (6 mice, given a commercially available gadodiamide bulk drug, the concentration of gadodiamide was 0.5 mg/ml, and the dosage was 10 ml/kg), the fibronectin-gadodiamide-cerasome group (6 mice, given a commercially available gadodiamide bulk drug, the concentration of gadodiamide was 0.5 mg/ml, and the dosage was 10 ml/kg), the selectin-gadodiamide-cerasome group (6 mice, given a commercially available gadodiamide bulk drug, the concentration of gadodiamide was 0.5 mg/ml, and the dosage was 10 ml/kg), and the osteopontin-gadodiamide-cerasome group (6 mice, given a commercially available gadodiamide bulk drug, the concentration of gadodiamide was 0.5 mg/ml, and the dosage was 10 ml/kg). Animals in each experimental group were injected with the corresponding tracer through the tail vein, and MRI imaging was performed before administration and at multiple time points after administration to observe the identification of atherosclerotic vulnerable plaque in each group.

Figure 19:
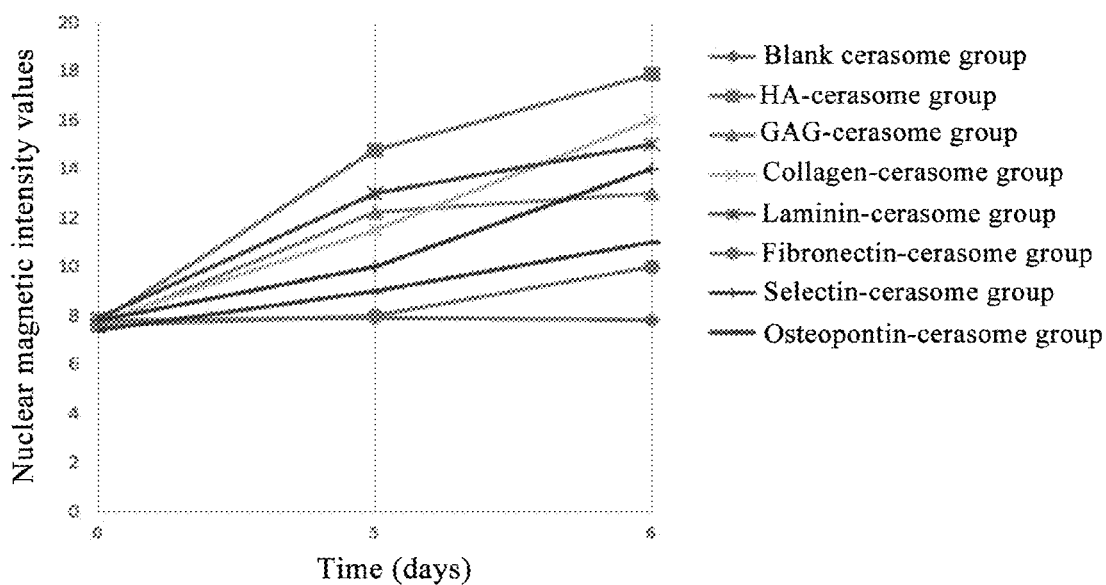
FIG. 19 shows the in vivo MRI tracing of various CD44 ligands-cerasome-gadodiamide delivery system for arterial vulnerable plaques.

Experimental Results:

FIG. 19 displays the in vivo tracing effect of the cerasome delivery system of the present disclosure with multiple CD44 ligands as probes on arterial vulnerable plaques. As shown in the figure, compared with the blank cerasome group, administration with the cerasome nano system of the present disclosure having multiple CD44 ligands (including HA, collagen, laminin, fibronectin, selectin, osteopontin) as targeting probes may show recognition effect on arterial vulnerable plaques, resulting in a better MRI tracing effect.

Example 12: Tissue Distribution of HA-Cerasome of Various Particle Sizes-Iodixanol Delivery System of the Present Disclosure The purpose of this example is to verify the tissue distribution of the cerasome nano delivery system of the present disclosure (of various particle sizes) which is loaded with a CT tracer.

Experimental Method:

(1) A commercially available raw material iodixanol was used, and the cerasome nano delivery system of various particle sizes (having HA molecular weight of 100,000 Da) was prepared by the following method:

(2) A mouse model of atherosclerotic vulnerable plaque was constructed according to the method described in Example 6 above.

(3) The model mice were fed with a high-fat diet (same as in Example 6) for 16 weeks. 36 model mice were randomly divided into the cerasome group with a particle size of 280 nm (12 mice), the cerasome group with a particle size of 200 nm (12 mice), and the cerasome group with a particle size of 160 nm (12 mice), wherein the carrier was loaded with a commercially available iodixanol bulk drug, and the concentration of iodixanol was 0.5 mg/ml, and the dosage was 10 ml/kg. Animals in each experimental group were injected with the corresponding tracer through the tail vein, and tissue collection was performed before administration and at 4 time points (3 animals per time point) after administration to observe the tissue distribution of iodixanol in each group of animals.

Experimental Results:

Table 3 displays the tissue distribution of the cerasome nano delivery systems of the present disclosure of various particle sizes which are loaded with a CT tracer. As shown in the table, the cerasome of 200 nm described in the present disclosure can be better enriched in arterial vulnerable plaques compared to cerasome groups of other particle sizes.

TABLE 3

| | Concentration in tissue after single intravenous injection of cerasome of various particle sizes | | | | | | | | |
|---|---|---|---|---|---|---|---|---|---|
| Time | 280 nm cerasome group | | | 200 nm cerasome group | | | 160 nm cerasome group | | |
| (h) | Spleen | Liver | Plaque | Spleen | Liver | Plaque | Spleen | Liver | Plaque |
| 2.00 | 2370 | 1812 | 121 | 1570 | 1743 | 134 | 1236 | 1617 | 109 |
| 4.00 | 2033 | 1219 | 50 | 1523 | 1002 | 55.8 | 1198 | 918 | 43 |

TABLE 3-continued

Concentration in tissue after single intravenous injection of cerasome of various particle sizes

| Time | 280 nm cerasome group | | | 200 nm cerasome group | | | 160 nm cerasome group | | |
|---|---|---|---|---|---|---|---|---|---|
| (h) | Spleen | Liver | Plaque | Spleen | Liver | Plaque | Spleen | Liver | Plaque |
| 8.00 | 1290 | 387 | ND | 870 | 315 | ND | 652 | 321 | ND |
| 24.0 | 791 | 89 | ND | 557 | 61.8 | ND | 461 | 77 | ND |

Example 13: Tissue Distribution of HA of Various Molecular Weights-Cerasome-Iodixanol Delivery System of the Present Disclosure The purpose of this example is to verify the tissue distribution of the cerasome nano delivery system loaded with a CT tracer and having HA (with various molecular weights) as a recognizing ligand of the present disclosure.

Experimental Method:

(1) A commercially available raw material iodixanol was used, and the cerasome nano delivery system (with a particle size of 200 nm) was prepared by the following method: 1 g of sodium hyaluronate HA1, HA2, and HA3 (having a molecular weight of 200,000 Da, 100,000 Da, and 30,000 Da respectively) were completely dissolved in ultrapure water, respectively, and 0.1 g of 1-(3-dimethylaminopropyl)-3-ethylcarbodiimide hydrochloride (EDC·HCl) and 0.12 g of N-hydroxysulfosuccinimide (sulfo-NHS) coupling agent were added to activate the carboxyl group. After stirred at room temperature for 1 hour, acetone was added to the reaction solution to precipitate the activated HA. The precipitation was filtered, washed with ethanol and dried in vacuo to give activated HA. The same is formulated to a 0.1 mg mL$^{-1}$ aqueous solution, and 0.2 mL of the solution was transferred and dissolved in the cerasome vesicle suspension obtained in the above step, for coupling the activated carboxyl group in the activated HA to the amino group of the DSPE molecule incorporated in the lipid bilayer of the cerasome vesicle via forming amide bonds, to obtain three cerasome delivery systems HA1-CL1@R, HA2-CL1@R and HA3-CL1@R, which were loaded with a therapeutic agent.

(2) A mouse model of atherosclerotic vulnerable plaque was constructed according to the method described in Example 6 above.

(3) The model mice were fed with a high-fat diet (same as in Example 6) for 16 weeks. 36 model mice were randomly divided into the HA1-CL1@R group (12 mice), the HA2-CL1@R group (12 mice), and the HA3-CL1@R group (12 mice), wherein the carrier was loaded with a commercially available iodixanol bulk drug, and the concentration of iodixanol was 0.5 mg/ml, and the dosage was 10 ml/kg. Animals in each experimental group were injected with the corresponding tracer through the tail vein, and tissue collection was performed before administration and at 4 time points (3 animals per time point) after administration to observe the tissue distribution of iodixanol in each group of animals.

Experimental Results:

Table 4 displays the tissue distribution of the HA of various molecular weights-cerasome nano delivery systems of the present disclosure which are loaded with a CT tracer. As shown in the table, the HA of 100,000 Da described in the present disclosure can be better enriched in arterial vulnerable plaques compared to HA of other molecular weight.

TABLE 4

Concentration in tissue after single intravenous injection of HA of various molecular weights

| Time | HA3-CL1@R group | | | HA2-CL1@R group | | | HA1-CL1@R group | | |
|---|---|---|---|---|---|---|---|---|---|
| (h) | Spleen | Liver | Plaque | Spleen | Liver | Plaque | Spleen | Liver | Plaque |
| 2.00 | 1330 | 1623 | 112 | 1570 | 1743 | 134 | 2336 | 1981 | 78 |
| 4.00 | 753 | 1198 | 51 | 1523 | 1002 | 55.8 | 1825 | 1384 | 42 |
| 8.00 | 490 | 652 | ND | 870 | 315 | ND | 1398 | 657 | ND |
| 24.0 | 54 | 192 | ND | 557 | 61.8 | ND | 879 | 102 | ND |

The various aspects of the disclosure have been exemplified by the above-described examples. Obviously, the above examples are merely examples used for clear description, instead of limiting the implementation modes. For a person skilled in the art, other forms of changes or variations may also be made on the basis of the above description. There is no need and no way to exhaust all implementation modes here. Obvious changes or variations resulting therefrom are still within the scope of the present disclosure.

The invention claimed is:

1. A cerasome delivery system for targeting an activated CD44 molecule, and wherein the cerasome delivery system comprises a cerasome vesicle, which is a closed vesicle formed by a lipid bilayer having an inner hydrophilic cavity, and wherein the surface of the vesicle has an inorganic polysiloxane reticulate structure, and wherein the lipid bilayer is formed by components including: a cerasome monomer molecule CL1 set forth by formula (I):

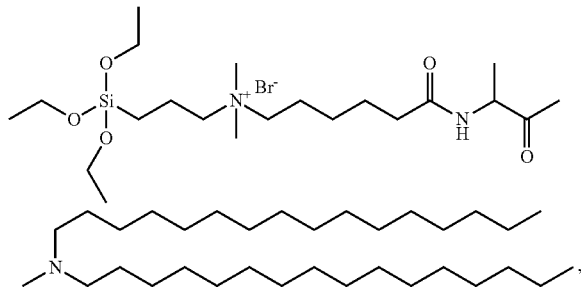

(I)

a distearoylphosphatidylethanolamine (DSPE) molecule, and distearoylphosphatidylcholine (DSPC), in a weight ratio of 5:2.5:1.5, wherein the DSPE molecule is coupled through the amino group thereof directly to a targeting ligand by an amide bond on the surface of the cerasome vesicle, and the targeting ligand is capable of specifically binding to the activated CD44 molecule.

2. The cerasome delivery system of claim 1, wherein the cerasome delivery system is for targeting a vulnerable plaque, and the targeting ligand is capable of specifically binding to a CD44 molecule on a cell surface at the vulnerable plaque.

3. The cerasome delivery system of claim 1, wherein the particle size of the cerasome vesicle is in the range of 50 nm-400 nm.

4. The cerasome delivery system of claim 1, wherein the targeting ligand is selected from glycosaminoglycan (G.A.G.), collagen, laminin, fibronectin, selectin, osteopontin (O.P.N.), and monoclonal antibodies HI44a, HI313, A3D8, H90, and IM7; or is selected from a hyaluronic acid or a hyaluronic acid derivative capable of specifically binding to a CD44 molecule on a cell surface at the vulnerable plaque.

5. The cerasome delivery system of claim 1, wherein the targeting ligand has a molecular weight of 10,000-400,000 Da.

6. The cerasome delivery system of claim 1, wherein the cerasome is loaded with a substance for diagnosing, preventing, and/or treating the vulnerable plaque or a disease associated with the vulnerable plaque.

7. The cerasome delivery system of claim 6, wherein the substance is selected from one or more of statins, fibrates, antiplatelet drugs, PCSK9 inhibitors, anticoagulant drugs, angiotensin converting enzyme inhibitors (ACEI), calcium ion antagonists, M.M.P.s inhibitors, β receptor blockers, pharmaceutically acceptable salts thereof, and active structure fragments thereof.

8. The cerasome delivery system of claim 7, wherein the substance for preventing and/or treating the vulnerable plaque or a disease associated with the vulnerable plaque is selected from one or more of lovastatin, atorvastatin, rosuvastatin, simvastatin, fluvastatin, pitavastatin, pravastatin, bezafibrate, ciprofibrate, clofibrate, gemfibrozil, fenofibrate, probucol, anti-PCSK9 antibodies, antisense RNAi oligonucleotides, nucleic acids, adnectin and the effective fragments or pharmaceutically acceptable salts thereof, one or more of pharmaceutically acceptable salts thereof, and active structure fragments thereof.

9. A medicament, comprising the cerasome delivery system of claim 1, and one or more pharmaceutically acceptable carriers.

* * * * *